(12) United States Patent
Hanko et al.

(10) Patent No.: US 9,095,850 B2
(45) Date of Patent: Aug. 4, 2015

(54) SYSTEM FOR TREATING LIQUIDS

(75) Inventors: Michael Hanko, Dresden (DE); Stefanie Honncher, Waldheim (DE); Axel Fikus, Hartha (DE)

(73) Assignee: Endress + Hauser Conducta Gesellschaft für Mess—und Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 13/634,274

(22) PCT Filed: Mar. 23, 2011

(86) PCT No.: PCT/EP2011/054408
§ 371 (c)(1),
(2), (4) Date: Sep. 12, 2012

(87) PCT Pub. No.: WO2011/117275
PCT Pub. Date: Sep. 29, 2011

(65) Prior Publication Data
US 2013/0000417 A1    Jan. 3, 2013

(30) Foreign Application Priority Data

Mar. 25, 2010 (DE) .......... 10 2010 003 304
Jun. 24, 2010 (DE) .......... 10 2010 030 489
Feb. 3, 2011 (DE) .......... 10 2011 003 612

(51) Int. Cl.
*B01L 3/00* (2006.01)
*G01N 35/10* (2006.01)

(52) U.S. Cl.
CPC .......... *B01L 3/502715* (2013.01); *B01L 3/527* (2013.01); *G01N 35/1097* (2013.01); *B01L 2200/027* (2013.01); *B01L 2300/0867* (2013.01); *B01L 2300/123* (2013.01);
(Continued)

(58) Field of Classification Search
CPC .......... B01L 3/502715; B01L 3/527
USPC .......... 422/50, 500–503, 112–113; 436/180
See application file for complete search history.

(56) References Cited

U.S. PATENT DOCUMENTS 5,123,443 A    6/1992    Garrison
5,250,263 A    10/1993    Manz
(Continued)

FOREIGN PATENT DOCUMENTS

DE    90131932    4/1991
DE    69111776    2/1996
(Continued)

OTHER PUBLICATIONS

International Search Report, Jun. 30, 2011, The Netherlands.
(Continued)

*Primary Examiner* — Jyoti Nagpaul
(74) *Attorney, Agent, or Firm* — Bacon & Thomas, PLLC

(57) ABSTRACT

A system for treating liquids comprising: a fluidics unit having at least one functional unit; at least one liquid storage unit of the first type; at least one liquid storage unit of second type; a first liquid line; and a second liquid line, wherein a flow of liquid through the first liquid line directed from the fluidics unit to the liquid storage unit of first type is blocked, at least at times, by means of a first valve and a flow of liquid through the second liquid line in the direction from the liquid storage unit of second type to the fluidics unit is blocked, at least at times, by means of a second valve.

22 Claims, 9 Drawing Sheets

(52) U.S. Cl.
CPC . *B01L 2400/0478* (2013.01); *B01L 2400/0487* (2013.01); *B01L 2400/0605* (2013.01); *B01L 2400/065* (2013.01); *B01L 2400/0655* (2013.01); *Y10T 137/87153* (2015.04)

(56) References Cited

U.S. PATENT DOCUMENTS

| | | | |
|---|---|---|---|
| 5,447,692 | A | 9/1995 | Keenan |
| 6,238,910 | B1* | 5/2001 | Custance et al. ......... 435/287.2 |
| 6,432,696 | B2 | 8/2002 | Custance |
| 2001/0043882 | A1 | 11/2001 | Berger |
| 2005/0214165 | A1 | 9/2005 | Babel |
| 2007/0023641 | A1 | 2/2007 | Weitz |
| 2007/0048194 | A1 | 3/2007 | Schulein |
| 2008/0022786 | A1 | 1/2008 | Sann |
| 2009/0010820 | A1 | 1/2009 | Fehm |
| 2009/0053814 | A1 | 2/2009 | Patel |
| 2009/0126505 | A1 | 5/2009 | Shiraki |
| 2011/0236273 | A1 | 9/2011 | Claussen |
| 2012/0136491 | A1 | 5/2012 | Oberndorder |
| 2012/0173164 | A1 | 7/2012 | Steuerwald |

FOREIGN PATENT DOCUMENTS

| | | |
|---|---|---|
| DE | 69304542 | 1/1997 |
| DE | 10227032 | 11/2003 |
| DE | 10232593 | 1/2004 |
| DE | 102004001916 | 8/2005 |
| DE | 102004022423 | 12/2005 |
| DE | 69935230 | 12/2007 |
| DE | 202009007800 | 9/2009 |
| DE | 102008042581 | 4/2010 |
| DE | 102009029305 | 3/2011 |
| EP | 0484278 | 5/1992 |
| EP | 1156336 | 11/2001 |
| EP | 1941947 | 7/2008 |
| WO | WO 03/092893 | 11/2003 |
| WO | WO 03/096027 | 11/2003 |
| WO | WO 2006/115663 | 11/2006 |
| WO | WO 2007/021812 | 2/2007 |
| WO | WO 2007/117987 | 10/2007 |
| WO | WO 2008/030541 | 3/2008 |

OTHER PUBLICATIONS

German Search Report, Sep. 8, 2011, Munich.
German Search Report, Jun. 24, 2010, Munich.
English translation IPR, Oct. 4, 2012, WIPO, Geneva.

* cited by examiner

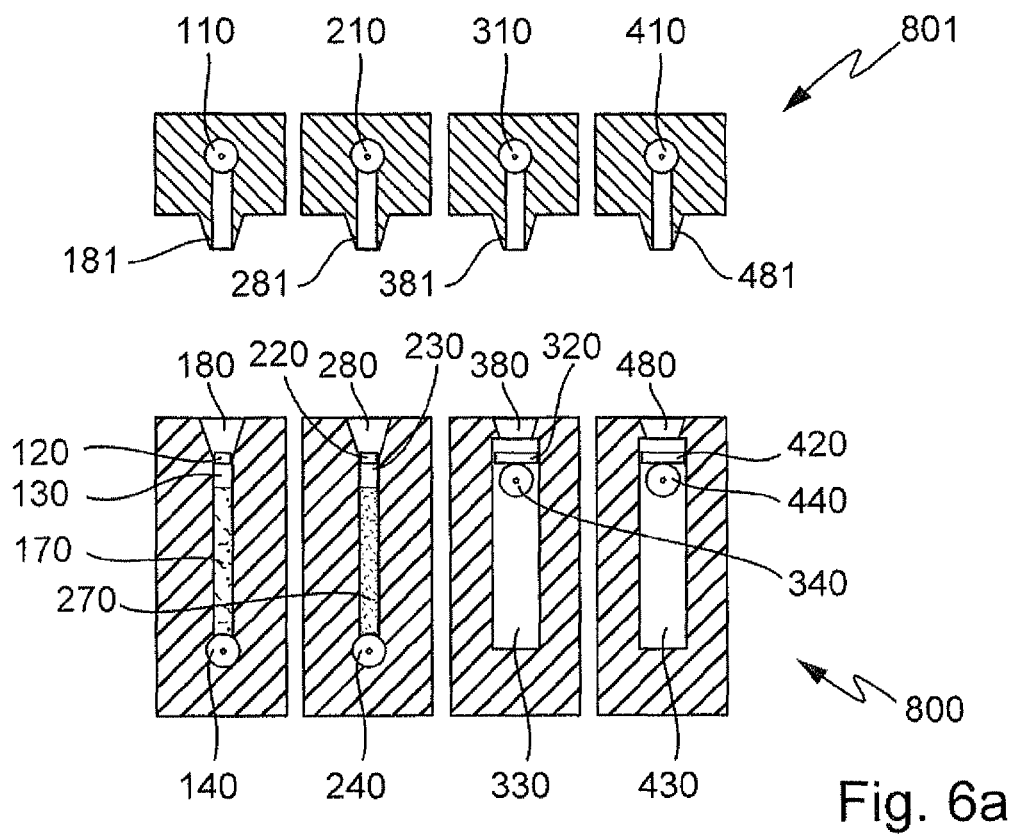
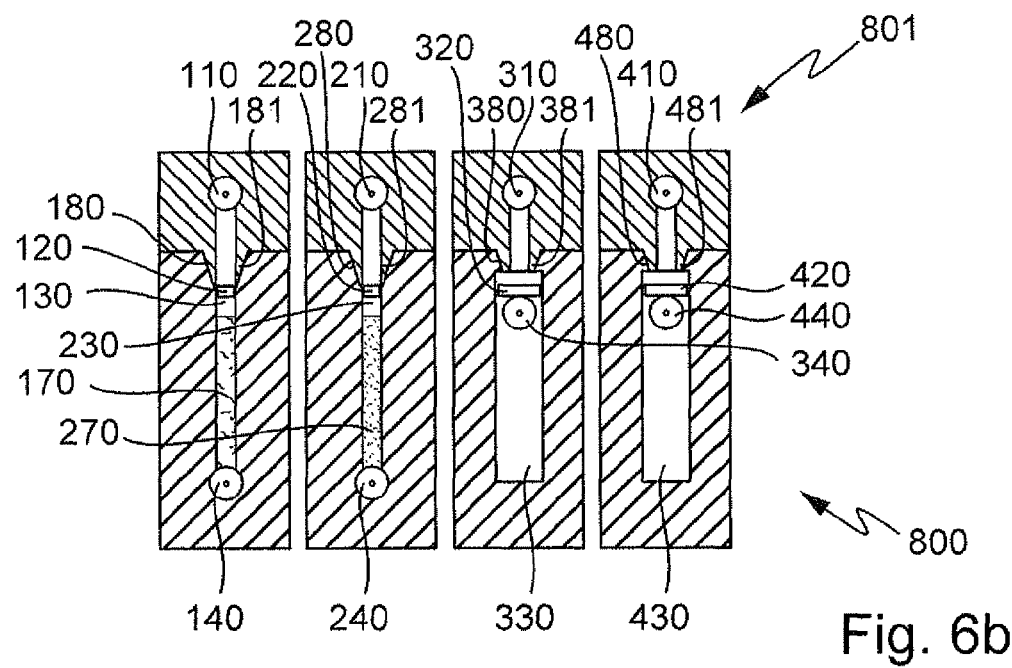
Fig. 6a
Fig. 6b

SYSTEM FOR TREATING LIQUIDS

TECHNICAL FIELD

The invention relates to a system for treating liquids, especially for application in analysis.

BACKGROUND DISCUSSION

Systems for treating liquids, especially for analysis, are applied, for example, in process measurements technology or in industrial measurements technology. For example, analytical systems can be applied for monitoring and optimizing the cleaning effectiveness of a clarification plant, for monitoring drinking water or for quality monitoring of food. Measured and monitored are, for example, the content of special substances in a liquid sample, for example, the content of ions, such as ammonium, phosphate or nitrate, or biological or biochemical compounds, such as hormones, or microorganisms, e.g. bacteria.

SUMMARY OF INVENTION

Frequently in analytical systems, the sample to be analyzed is mixed with one or more reagents, so that a chemical change occurs in the liquid sample, for example, due to a chemical reaction of the reagent with the substance to be monitored. Preferably, the reagents are so selected that the chemical change is detectable by means of physical methods, for example, by optical measurements. A simple example of such a chemical change can be a color change, which is detectable photometrically, thus with optical means. In the field of bioanalysis, frequently analytical methods are applied according to an assay principle. These rest on a specific binding ability of a binding partner with a biomolecule to be detected. Frequently, the binding partners are so selected that the molecule to be determined, also referred to as the analyte, and the binding partner form an antibody/antigen-system. With the help of physically detectable markers on the analyte, on the binding partner or on a competitor added to the system, which likewise can bind to the binding partner of the analyte, the amount of the specifically bound analyte molecules can be ascertained, and therefrom, the concentration of the analyte in the sample can be deduced. The markers can be in the form of, for example, luminescing molecules, luminescing nano particles or magnetic nano particles. Frequently, the binding partner, to which the analyte specifically binds, is immobilized on a surface; it can, however, also be present in solution.

In order to automate such analytical methods, for example, for industrial applications, it is necessary to provide an analytical system, which performs the desired analytical method automatically. The most important requirements for such an analytical system are, besides a sufficient accuracy of measurement, robustness, simple serviceability and the assurance of a sufficient working, and environmental, safety. Since the reagents used for the analysis are, in part, not directly returnable to the water system, their safe disposal likewise plays an essential role.

In the state of the art, there exist already a large selection of semiautomatic and automatic, analytical systems. Although many of these function without problem, they are frequently relatively complicated in construction, and, consequently, susceptible to defects and, as a rule, only serviceable by trained operating personnel. Thus, for example, DE 102 22 822 A1 discloses an online analyzer for analyzing a sample. The online analyzer is embodied in the form of a device that comes in a cabinet, in which are arranged a control unit, reagent supply containers, pumps for conveying reagents into a mixing cuvette for mixing the reagents with the liquid, a waste container, as well as an optical unit for optical measurements on the liquid sample treated in the mixing cuvette with reagents. The reagents are led via hose connections from the reagent containers and transported into the mixing cuvette. Correspondingly, used liquid is transferred from the mixing cuvette, again, via a hose connection into the waste container. If the waste container or one of the reagent supply containers must be replaced, attention must be paid that the hose connections are then reconnected correctly. The hoses and the conveyor pumps are susceptible to material fatigue and must likewise be subjected to maintenance or replaced from time to time.

Especially in the field of biosensors and medical technology, analytical systems have been developed, in the case of which the treating of the examined sample with reagents is performed by means of technologies, which are known from the technical field referred to generically as "lab on a chip". Frequently, the sample need only be applied to a prepared chip, which, besides liquid lines for the sample and for reagents, also includes reagent reservoirs as well as functional elements, for example, mixers or valves. The chip can, after application of the sample, be inserted into an analytical device, which performs and controls the treating of the liquid sample with the reagents and performs the corresponding physical measurements on the treated liquid sample. Such a device is described, for example, in US 2009/0126505 A1 or EP 967 266 A1. The chips disclosed there are embodied as single-use products, so that a new chip must be used for each analysis.

US 2009/0053814 A1 describes an analytical system with automatically fillable, internal reagent storage and a fluidics system for automatic treating of a liquid sample with the reagents as well as an optical measuring apparatus for detecting chemical changes in the treated sample. Also, this system with syringe pumps, fluidics connections between the pumps and the reagent containers, and valves for switching between an external reagent reservoir and an internal reagent storage is relatively complicated in construction and, thus, maintenance intensive and serviceable only by trained operating personnel.

It is therefore an object of the invention to provide, especially in an analytical system, a system for treating liquids overcoming the disadvantages of the state of the art. Especially, the system should satisfy requirements for use in process measurements technology, i.e. it should be able to perform a series of treatments, especially analyses, without parts having to be replaced in between. Also, it should be robust, economical and simple to service, especially it should also avoid the danger of contamination of an operator or the environment.

This object is achieved by a system for treating liquids, especially for analysis and/or synthesis of liquids, comprising:
- a fluidics unit having at least one functional unit;
- at least one liquid storage unit of first type;
- at least one liquid storage unit of second type;
- a first liquid line, which connects the at least one liquid storage unit of first type and the fluidics unit for supply of liquid from the liquid storage of first type into the fluidics unit; and
- a second liquid line, which connects the liquid storage of second type and the fluidics unit for draining liquid from the fluidics unit into the liquid storage of second type; characterized in that a flow of liquid through the first liquid line directed from the fluidics unit to the liquid storage of first type is blocked, at least at times, by means of a first valve, and that a flow of liquid through the second liquid line in the direction from the liquid storage of second type to the fluidics unit is blocked, at least at times, by means of a second valve.

Meant by 'a fluidics unit' is a system for handling, especially for conveying and for mixing, fluids, especially liquids, through one or more fluid lines, for example, liquid lines, wherein additional functional units can be provided. Special cases of fluidics units are microfluidics units. In these, the fluid lines and the functional units are miniaturized, which means that the fluid lines are channels with a cross section between $10^7$ and $1 \mu m^2$, preferably between $10^6$ and $10^2 \mu m^2$, further preferably between $10^5$ and $10^4 \mu m^2$.

A functional unit of a (micro-) fluidics unit can be, for example, a reaction container, or a mixing apparatus. A functional unit can also be a signal transducer of a sensor, for example, a surface, on which a layer of biochemical receptors is applied or appliable, on which a biomolecule to be detected in the sample specifically binds. Also, a chromatographic column, for example for HPLC, especially in combination with a detector, can form a functional unit.

The treating of a liquid means especially mixing it with reagents, for example, for performing a chemical reaction, wherein the liquids and the reagents can be pure liquids, liquid mixtures, solutions, emulsions or suspensions. A treating of liquids can also comprise an analysis. Furthermore, a treating of liquids can also mean conducting two or more liquids, one after the other, through a functional unit, for example, in order, in a first step, to activate a surface of the functional unit by immobilizing on the surface binding partners contained in a first liquid for an analyte to be determined, and, in a second step, to conduct a sample, which contains the analyte, into the so prepared functional unit.

The system can have one or more liquid storage units of a first type and one or more liquid storage units of a second type. The one or more liquid storage units of the first type contain liquids, which are to be introduced into the fluidics unit. They are, as a rule, "supply containers" for reagents, regenerating- or cleaning liquid for regeneration e.g. of functional units of the fluidics unit, or for cleaning the fluidics unit. A liquid storage unit of the first type can also serve as a buffer for the sample to be analyzed, which is, first of all, removed from a process vessel, for example, a pipeline, and, thereafter, filled into the liquid storage unit of the first type. This can occur automatically, for example, by means of pneumatic sample taking. The liquid storage unit of the first type provided for the sample includes therefor a connection for a sample supply line and a connection for a liquid line, via which the sample can be fed to the fluidics unit. The one or more liquid storage units of the second type serve to receive liquids from the fluidics unit. They are, as a rule, "waste containers", which receive the treated and analyzed liquid samples, which, in given cases, were mixed with reagents.

If the system comprises a number of liquid storage units of the first type and/or a number of liquid storage units of the second type, each of which is connected via a liquid line with the fluidics unit, it is advantageous to block by means of first valves, at least at times, a flow of liquid through the liquid lines connecting the liquid storage unit of the first type with the fluidics unit in the direction from the fluidics unit to the liquid storage unit of the first type, and to block by means of second valves, at least at times, a flow of liquid through the liquid lines connecting the liquid storage unit of the second type with the fluidics unit in the direction from the liquid storage unit of the second type to the fluidics unit. The first valves are arranged for this, in each case, in the flow path between a liquid storage unit of the first type and the fluidics unit. The second valves are arranged correspondingly, in each case, in the flow path between a liquid storage unit of the second type and the fluidics unit. In such case, the first and second valves can be arranged in a liquid line, in the fluidics unit itself or in the region of a connection of the liquid storage unit to the liquid line.

Flow of liquid from the at least one liquid storage unit of the first type through the first liquid line into the fluidics unit and/or from the fluidics unit through the second liquid line in the at least one liquid storage unit of the second type can be produced pneumatically. For this, the liquid storage units, especially all liquid storage units of the system can be providable with pressure. The pressure loading of the liquid storage unit can occur by means of a controllable pneumatic pressure source of a pneumatic system connected to the liquid storage units via the pneumatic lines. The pressure source can be connected with the pneumatic lines via controllable valves. Thus, it is possible, with targeting, to apply predetermined pressure differences stably to the liquid storage units, in order to transport liquid through the liquid lines to, and from, the fluidics unit and also through a complicated channel structure within the fluidics unit.

In a first variant, the valves can be pneumatically actuatable valves, which are also referred to as pneumatically actuated valves. These valves can, depending on need, be opened for letting liquid flow in the respective flow path. In order to block the flow of liquid on the flow path, the pneumatically actuated valves can be correspondingly closed. For this, the system includes corresponding pneumatic lines connected with the pneumatically actuated valves. Via these pneumatic lines, a pressure source, for example, a pressure source of the pneumatic system can actuate the pneumatically actuated valves. The pressure source can be the same pressure source that also effects the liquid transport from the one or more liquid storage units of first type into the one or more liquid storage units of the second type.

The pneumatically actuated valves can be embodied in many different ways. For example, they can be embodied as normally open valves, i.e. be so embodied that they are open in their unactuated, rest position and closed when a pressure is applied via the pneumatic line connected with the valve. Advantageously, the pneumatically actuated valves can be embodied as normally closed valves, i.e. be so embodied that they are closed in their unactuated, rest position and open when a pressure is applied via the pneumatic line connected with the valve. If a number of liquid storage units of the first type are present, which are connected with the fluidics unit via liquid lines, so that, in each case, a flow path for liquids from each liquid storage unit into the fluidics unit is formed, a pneumatically actuatable valve is correspondingly arranged in each flow path. In the same way, in case a number of liquid storage units of the second type are present, which are connected with the fluidics unit via liquid lines, so the, in each case, a flow path for liquids from the fluidics unit into the liquid storage unit of the second type is formed, a pneumatically actuatable valve is arranged in each flow path.

The at least one liquid storage unit of the first type can have an interface for the connection of a pneumatic line, via which the liquid storage unit of the first type is loadable with pressure, in order to transport the liquid contained in the liquid storage unit in the direction of the fluidics unit, wherein the pneumatic line is supplementally connected with the pneumatically actuated, first valve, so that a pressure loading of the liquid storage unit of the first type simultaneously acts on the pneumatically actuated, first valve. The pneumatically actuated, first valve is here preferably embodied as a normally closed valve. If the liquid storage unit of the first type is supplied with pressure via the pneumatic line, the pneumatically actuated, first valve opens simultaneously, so that liquid can flow from the liquid storage unit of the first type into the fluidics unit. If a number of liquid storage units of the first type are present, preferably all these liquid storage units have an interface for the connection of a pneumatic line, via which they are loadable with pressure, especially, in each case, independently from one another, in order to transport the liquid contained in the liquid storage units into the fluidics unit. In the flow path after each liquid storage unit of the first type, there is then preferably arranged a pneumatically actuated valve, which is normally closed. The pneumatic lines connected with the interfaces of the liquid storage units are advantageously, supplementally, connected in each case with the valve belonging to the respective liquid storage unit, so that a pressure loading of a liquid storage unit, in each case, simultaneously opens the associated valve and liquid can flow from the liquid storage unit into the fluidics unit. The pressure loading of the liquid storage units via pneumatic lines can occur, for example, by means of the above mentioned controllable pneumatic pressure source connected via the pneumatic lines to the liquid storage unit. The valves belonging to the liquid storage units can also be components of the liquid storage unit and advantageously are produced as a single assembly, for example, using injection molding technology.

The liquid transport from the liquid storage units of the first type into the fluidics unit, or from the fluidics unit into the liquid containers of the second type can occur by pressure loading of one or more liquid containers of the first type, when applied to the one or more liquid containers of the second type is a pressure, which is less than the pressure applied to the liquid containers of the first type for the liquid transport. Especially, atmospheric pressure can be applied to the liquid containers of the second type. In this case, the liquid containers of the second type then require no interface for the connection of pneumatic lines. For blocking the flow of liquid from a liquid storage unit of the second type toward the fluidics unit, there can be arranged in the flow path between the fluidics unit and at least one, especially each, liquid storage unit of the second type a normally closed, second valve, which is opened by pressure loading, so that liquid can flow from the fluidics unit into the liquid storage unit of the second type. Also, in this case, for each combination of valve and liquid storage unit of the second type, only one pneumatic line is required, in order to open or to block the corresponding liquid path. Also, in this case, a shared assembly, which both includes the valve as well as also the liquid storage unit of the second type, can be provided. Since, thus, for each combination of liquid storage unit and belonging pneumatically actuated valve, a single pneumatic line is sufficient for pressure loading, in order to transport liquids through the system, the embodiment of the system with pneumatically actuated valves is not more complex than that with check valves. In both cases, per liquid storage unit, only one pneumatic line is required, as will become yet more evident below in connection with the description of the figures. This has advantages compared to an embodiment, in the case of which the liquid transport occurs through pump systems or pneumatic- or hydraulic means and supplementally valves must be actuated. In the case of the system of the invention, only a relatively low number of pneumatic connections are required for pressure loading of the liquid storage units, respectively valves, in order to bring about liquid transport into and from the fluidics unit and to perform in the fluidics unit treating steps, such as e.g. passing through cleaning- or calibration media, passing through samples and/or reagents and the mixing of liquids. This lessens, not least of all, especially the complexity of the automated control unit of the system.

Alternatively, the valves can be actuatable electrically or hydraulically instead of pneumatically. This increases, however, the control complexity and the complexity of the construction, as above described.

In a second variant, the valves can be check valves. A check valve, also referred to as a one way valve, generally blocks the passage of a medium, especially a liquid, in a direction, which is also referred to in the following as the blocking direction, while it permits passage in the opposite direction, which is also referred to in the following as the pass through direction. Usually, check valves are so embodied that a minimum pressure, which is referred to as the breakthrough pressure or opening pressure, is required, in order that the valve can allow the liquid to flow in the pass through direction.

In order that a first check valve thus prevents flow of a liquid from the fluidics unit to the at least one liquid storage unit of the first type, the first check valve is so arranged in the flow path between the liquid storage unit of the first type and the fluidics unit that its pass through direction points in the flow path from the liquid storage unit to the fluidics unit, while its blocking direction points correspondingly in the opposite direction. If there are a number of liquid storage units of the first type present, which are connected with the fluidics unit via liquid lines, so that, in each case, a flow path for liquids is formed from each liquid storage unit to the fluidics unit, then, correspondingly, a check valve with such orientation is arranged in each flow path.

In order that, correspondingly, the second check valve blocks flow of liquid from the at least one liquid storage unit of the second type to the fluidics unit, the second check valve is so arranged in the flow path between the fluidics unit and the liquid storage unit of the second type that its pass through direction in the flow path points from the fluidics unit to the liquid storage unit of the second type, while its blocking direction points, correspondingly, in the opposite direction. If there are a number of liquid storage units of the second type present, which are connected with the fluidics unit via liquid lines, so that, in each case, a flow path for liquids from the fluidics unit into each of the liquid storage units of the second type is formed, a check valve with such orientation is correspondingly arranged in each flow path.

The providing of check, which prevent flow of liquid through the first liquid line from the fluidics unit to the liquid storage unit of the first type, or flow of liquid through the second liquid line in the direction from the liquid storage unit of the second type to the fluidics unit, permits a very simple, efficient and robust control of the liquid transport through the fluidics unit. A check valve arranged between a liquid storage unit of the first type and the fluidics unit and blocking in the direction of the liquid storage unit of the first type prevents, on the one hand, the running back of liquid from the fluidics unit into the liquid storage, and, on the other hand, due to the required breakthrough pressure, avoids that, alone due to the hydrostatic pressure of the liquid in the liquid storage unit, liquid can flow uncontrolled into the fluidics unit device. Check valves arranged between the fluidics unit and a liquid storage unit of the second type assure that no liquid from the liquid storage unit of the second type can get back into the fluidics unit.

Both in the here described first variant with pneumatically or otherwise actuatable valves as well as also in the second variant with check valves, liquid from a liquid storage unit of the first type can be transported into the fluidics unit by arranging for a pressure difference between the liquid storage unit of the first type and a liquid storage unit of the second type. In the case where check valves are used, this pressure difference must be high enough that the breakthrough pressure of the check valve between the liquid storage unit of the first type and the fluidics unit is overcome. At the same time, on all other liquid storage units of the second type, a pressure is placed, which equals the pressure on the liquid storage unit of the first type, so that between the remaining liquid storage units of the second type and the liquid storage unit of the first type no pressure difference is present. In this way, the liquid is conveyed on a predetermined flow path through the fluidics unit between the liquid storage unit of the first type and the liquid storage unit of the second type. The check valves assure that no liquid from the remaining liquid storage units of the second type reaches the fluidics unit. Preferably, the check valves block, besides the flow of liquid, simultaneously the flow of gas, so that, for example, in the case of applying a pressure difference between liquid storage units of the first and the second type by means of a pneumatic system, no gas, e.g. pressurized air of the pneumatic system, can get from the liquid storage units into the fluidics unit reach.

Thus, alone by applying pressure differences between liquid storage units of the first type and liquid storage units of the second type, very efficiently, liquid can be transported through the fluidics unit, without requiring active functional elements, especially actuatable components such as valves or pumps, within the fluidics unit. The fluidics unit is therewith economical, robust and, as yet to be presented below, easy to maintain, or to replace. Especially, it is thereby facilitated that the fluidics unit, as a replaceable, single-use component, which after one time or multiple use for treating liquids, for example, for performing one or more liquid analyses, can be completely disposed of and replaced by a new, equally embodied, fluidics unit. Since due to the check valves, or pneumatically actuatable valves, arranged, in each case, between the liquid storage units and the fluidics unit, no danger exists that liquid or gas gets undesirably from the liquid storage units into the fluidics unit, the liquid storage units can be embodied with relatively large volume, so that an entire series of measurements can be performed, before a replacement or a new filling of the liquid storage units is required. Such a system for treating liquids can, for these reasons, be very advantageously applied in process technology for monitoring a liquid measured medium, for example, for monitoring the quality of drinking water or for monitoring a food, biotech or pharmaceutical process.

In an advantageous further development of the above described embodiment of the system with check valves, each check valve is so designed that, for opening the check valve in the pass through direction, the presence of a pressure difference is required, which is greater than or equal to a breakthrough pressure of the check valve, and wherein the breakthrough pressure of the first check valve, thus of that check valve, which blocks flow of liquid through the first liquid line in the direction from the fluidics unit to the liquid storage unit of the first type, is preferably greater than the breakthrough pressure of the second check valve, thus of that check valve, which blocks flow of liquid through the second liquid line in the direction from the liquid storage unit of the second type to the fluidics unit.

In the case of the liquid storage units of the first type, the hydrostatic pressure of the liquid acts in the pass through direction on the check valve. In order to be able to provide an as large as possible liquid storage unit of the first type, it is therefore advantageous to embody the check valve such that a relatively high breakthrough pressure is required, in order to open the check valve. In the case of the liquid storage units of the second type, the hydrostatic pressure of the liquid acts in the blocking direction of the check valve. Thus, it is sufficient to provide a smaller breakthrough pressure. The smaller the breakthrough pressure of the check valves, which block a flow of liquid or gas from the liquid storage unit of the second type back into the fluidics unit, the smaller the pressure difference need be, which must be placed between a liquid storage unit of the first type and a liquid storage unit of the second type, in order to transport liquid via a flow path between the two liquid storage units through the fluidics unit. Correspondingly small is the pressure loading of the liquid lines, which form this flow path, which means a longer lifetime and better state of sealing of the system, especially the fluidics unit.

In an advantageous embodiment, the system comprises individual replaceable modules, wherein a first replaceable module has the fluidics unit, at least one liquid supply line to the fluidics unit and at least one liquid discharge line from the fluidics unit, and wherein a second replaceable module comprises the at least one liquid storage unit of the first type and an interface for connecting the at least one liquid storage unit of the first type to the at least one liquid supply line to the fluidics unit. This interface is referred to below also as the fluidics interface for short. In a special embodiment, the second module can supplementally include the at least one liquid storage unit of the second type. Especially, the second module can have a number of liquid storage units of the first type and a number of liquid storage units of the second type. Correspondingly, the fluidics interface serves then for connecting all present liquid storage units of the first and second types to associated liquid lines, which connect the liquid storage units with the fluidics unit. The liquid lines connectable to the liquid storage unit of the first type serve as liquid supply lines to the fluidics unit, while the liquid lines connectable to the liquid storage unit of the second type serve as liquid drains from the fluidics unit.

The second replaceable module can, in turn, be composed of a plurality of replaceable individual modules, e.g. of individual liquid cartridges, which include, in each case, a liquid storage unit of the first type or the second type.

The expression 'replaceable module' means a module, which can be connected via one or more connections with another unit, especially another replaceable module, and then later be disconnected from such, in order that it can be replaced by a module of the same type. Modules have equal connections, so that each of them can be connected with the other unit, and then later disconnected, without any modifications. Preferably, modules of the same type also have housings with identical geometry, especially identical dimensions. Thus, modules of the same type have the same space requirement, and therefore can be replaced by one another without other changes of the remaining construction of the analytical system. Modules of the same type can differ, however, especially in the number of contained liquid storage units, functional units and/or fluid lines, especially also in the embodiment of the routing of the fluid lines, for example, the number of branchings between fluid lines, and the supply volume of a liquid storage unit. Thus, for example, an entire series of first modules of the same type can exist, which are designed for very different analytical methods, but which conform completely as regards their connections and space requirements. Therewith different first modules can be connected to one and the same second module, and, when required, be replaced by one another.

The described modular construction, furthermore, permits, in a very simple manner, the second module with the liquid storage units to be separated from the first module with the fluidics unit, when, for example, one or more liquid storage units are empty after performing a series of analyses. The second module can be replaced by a new, completely filled module of the same type. This greatly simplifies the maintenance of the analytical system for the operator. Also, such modular construction is of great advantage for the manufacturer. Thus, for example, a series of first modules of the same type with very differently constructed fluidics units and a series of second modules of the same type with different numbers of liquid storage units for different reagents can be provided. In this way, the manufacturer can have a "kit", from which to build a variety of combinations of fluidics units and liquid storage units with different combinations of reagents.

The modules can be embodied, for example, as single-use components, also referred to as disposables, which can be disposed of after use. This is especially advantageous for applications in biotechnology, in the case of which a reconditioning of the modules by cleaning and sterilization, respectively cleaning, sterilization and refilling of the modules, which include liquid storage units, would be much more expensive than the costs incurred by disposal and replacing the modules embodied as single-use components. As modules embodied as single-use components are preferably embodied especially simply and can be produced, for example, using injection molding technology.

The second module can include the first valve, which blocks flow of liquid and, in given cases, gas through the first liquid line from the fluidics unit to the liquid storage unit of the first type, and the second valve, which blocks flow of liquid and, in given cases, gas through the second liquid line from the liquid storage unit of the second type to the fluidics unit. The first and the second valve can especially be a first and a second check valve or a first and a second pneumatically actuated valve. If the second module has a number of liquid storage units of the first type and/or a number of liquid storage units of the second type, which are connected via liquid lines with the fluidics unit, advantageously, a flow of liquid through the liquid lines connecting the liquid storage units of the first type with the fluidics unit, from the fluidics unit to the liquid storage units of the first type, is blocked by means of valves, especially first check valves or first pneumatically actuated, normally closed valves, and a flow of liquid and, in given cases, gas through the liquid lines connecting the liquid storage units of the second type with the fluidics unit, from the liquid storage unit of the second type to the fluidics unit, is blocked by means of second valves, especially second check valves or second pneumatically actuated, normally closed valves. The first valves are arranged for this, in each case, in the flow path between a liquid storage unit of the first type and the fluidics unit, and the second valves are correspondingly arranged, in each case, in the flow path between a liquid storage unit of the second type and the fluidics unit. Advantageously, all first and second valves are components of the second module. In this way, the fluidics unit arranged in the first module can be embodied completely free of valves or other active functional elements, especially actuatable functional elements. This makes the first module with the fluidics unit especially economical and little susceptible to defects. Such an embodiment is, therefore, especially favorable for a first module provided as a single-use (disposable) component.

The second module can, furthermore, have another interface for connecting at least each liquid storage unit of the first type, especially each liquid storage unit, to, in each case, a pneumatic line of a pneumatic system. If the second module has pneumatically actuatable valves, these are likewise connected with the pneumatic system via this interface for actuation of the valves. This other interface is referred to in the following, for short, as the pneumatic interface. The pneumatic system serves to supply the liquid storage units and, in given cases, the pneumatically actuated valves, in each case, with predetermined pressure and so to transport liquid within the fluidics unit, as described above. Preferably, the pneumatic system is embodied in such a manner that the pressure reigning in each pneumatic line is individually adjustable, especially controllable. For this, the pneumatic system includes, for example, one or more controllable pneumatic pressure sources, which, in each case, is connected to the liquid storage unit via a pressure supply line equipped with a controllable valve. Thus, it is possible, with targeting, to apply predetermined pressure differences stably to the liquid storage units, in order to transport the liquid through the liquid lines to, or from, the fluidics unit and also via a complex duct structure within the fluidics unit.

The interface for connecting at least each liquid storage unit of the first type, especially each liquid storage unit, in each case, to a pneumatic line can comprise a closure element, for example, a diaphragm, a membrane or a filter, which seals the liquid storage units liquid tightly, but gas permeably, especially sealed against the penetration or escape of microorganisms or the escape of liquid from the liquid storage units. The diaphragm, the membrane or the filter can be arranged, for example, at a pneumatic connection end of the liquid storage unit. In this way, the liquid contained in a liquid storage unit is isolated from the environment. If the pneumatic lines are disconnected from the second interface, no liquid can escape from the liquid storage units and contaminate the environment. This is especially important in the case of analysis of biological samples, where, in given cases, microorganisms dangerous for the environment or for operators can be present.

In an advantageous embodiment of the system for treating liquids, the liquid within the at least one liquid storage unit of the first type and/or the at least one liquid storage unit of the second type is contained in a flexible, gaseous- and liquid impermeable containment, which is connected to the first liquid line.

Involved in such case can be, for example, a bag of a flexible material, such as, for example, a film of synthetic material, e.g. of polyethylene or polypropylene, contained in the respective liquid storage unit. In the case of this embodiment, likewise, the escape of liquid into the environment, in the case of replacement of the liquid storage unit, i.e., in the case of the disconnecting the pneumatic lines of the second interface or by evaporation, is prevented. Additionally, also contamination of the liquid contained in the bags by externally penetrating substances or microorganisms, however, also the exit of health- or environmentally endangering substances from the liquid storage units into the environment, can be safely prevented thereby. A further advantage of this embodiment is that forming gas bubbles in the liquid through the mixing of gas of the pneumatic system with liquid present in the liquid storage unit is prevented. Through the elimination of filter- or membrane elements in the second interface, additionally, a faster response can be effected, since pressure changes in the pneumatic line are transmitted faster to the liquid to be transported due to the smaller resistance. Moreover, this embodiment provides a greater freedom of choice for the material of the liquid storage unit, since this no longer comes in contact with the liquid, so that there is no longer the concern of its chemical durability or biocompatibility for biological samples. Also, the reconditioning of a replaceable module containing one or more liquid storage units is facilitated in this embodiment.

The above described modular construction of the system for treating liquids permits very simple maintenance. In the case of need for maintenance, for example, when one or more liquid storage units of the first type is /are completely emptied or when one or more liquid storage units of the second type is/are completely filled, an operator need only disconnect the second module from the pneumatic line via the second interface. In such case, the second module preferably remains connected with the first module. In the disconnecting of the second interface, no liquid or microorganisms can escape from the liquid containers into the environment. The removal of the second and first modules from the pneumatic unit is, thus, completely without danger for the operator.

Advantageously, the first and second modules are accommodated in a shared housing, for example, in the form of a cassette, which, besides a pneumatic interface, has just one other connection, namely a connection for the supplying of a sample from a sample supply in a liquid storage unit of the cassette. This cassette can in the manner of a printer cartridge of a conventional ink jet printer be easily removed by separating of the pneumatic interface and the samples connection by the operator and replaced by a new, especially equally constructed, cassette of the same type, whose liquid storage unit of the first type is filled and which liquid storage unit of the second type is empty. The used cassette can either be disposed of as a single-use (disposable) component or reconditioned by cleaning the first module with the fluidics unit and filling the liquid storage units in the second module anew, coupled with emptying liquid to be disposed of. The reconditioning of a used cassette need not be performed by the operator of the analytical system. It can be done by trained personnel, especially, in fact, by the manufacturer. In an advantageous embodiment, the cassette, preferably together with the container, from which a sample to be analyzed can be removed and, in given cases, placed in a liquid storage unit of the cassette, can be sterilized (autoclaved) by means of superheated steam. The system for treating liquids can be, for example, an analyzer embodied to withdraw a sample from a process, for example, a biotechnological process for manufacturing a chemical or pharmaceutical product, and to analyze such sample relative to one or more parameters. In such case, it is advantageous, after terminating the process, to sterilize the process apparatus and the connected system, including the cassette, especially by means of superheated steam. After the sterilizing, the cassette can be removed and disposed of. Even when the cassette is destroyed in connection with its disposal, no damaging microorganisms can get into the environment, due to the earlier performed sterilization.

In an advantageous embodiment, the system includes at least one flow path for the transport of liquid from one or more liquid storage units of the first type through the fluidics unit into a liquid storage unit of the second type, wherein the system includes a measuring arrangement for determining a flow, especially a mass- or volume flow, of the liquid in the flow path. Flow sensors can be provided at suitable points of the flow path for this. The system can, moreover, include other sensors, for example, temperature sensors, which can be arranged in the region the fluidics unit or the liquid storage units.

The system can furthermore have a control unit, which is embodied, based on at least one of measured values provided by the measuring arrangement, to control the pressure in at least one of the pneumatic lines of a pneumatic system connected to the liquid storage units of the first and the second type. The control unit is, for example, an electronic data processing unit, e.g. a programmable logic controller having a processor and a data memory. While the liquid storage units and the fluidics unit can as described above be embodied as replaceable modules, the control unit and the pneumatic system are preferably fixed components of the system and can, for example, be durably integrated into a housing structure, into which the replaceable modules are insertable. The control unit can furthermore be embodied for evaluation of data of other sensors of the system and for display of information and measured values.

In order to perform successive guiding of various liquids through a functional unit or a mixing of two liquids in the fluidics unit, the fluidics unit can have, for example, a first liquid line section connected with a first liquid storage unit of the first type and a second liquid line section connected with a second liquid storage unit of the first type, wherein the first and the second liquid line sections combine at a first point to a third liquid line section, which, at a second point remote from the first point, branches into fourth and fifth liquid line sections, wherein at least the fourth liquid line section opens into a functional unit, and wherein from the functional unit at least a sixth liquid line section leads away, which is connected with a first liquid storage unit of the second type, and wherein the fifth liquid line section is connected with a second liquid storage unit of the second type.

This is a basic structure, which can always be used, when two liquids from two separate liquid storage units of the first type to be mixed or transferred one after the other into a functional unit. Of course, the fluidics unit can comprise significantly more liquid lines and liquid line sections, for example, in order to mix in other reagents or in order to conduct other liquids through the fluidics unit, e.g. for cleaning- or regeneration purposes. Moreover, other functional units can be provided, for example, in order to detect different analytes within one and the same sample, or to expose a sample to a multistage treatment.

The fluidics unit can be embodied as a microfluidics unit, in order in each analysis to use as little volume of reagents as possible. The microfluidics unit, which can be embodied, for example, as a microfluidics chip, includes, in such case, at least one functional unit and at least one microfluidic channel or microchannel leading as liquid supply line to the functional unit and at least one microfluidic channel or microchannel leading as liquid discharge line away from the functional unit.

Preferably, the fluidics unit of the system has only passive means for controlling the liquid flow, such as, for example, the previously described branching or rejoining ducts, or duct sections. Especially, the first module, which includes the fluidics unit, contains no valves or other actuatable, functional elements. In this way, there is assured, on the one hand, a very simple and therewith little defect susceptible, liquid transport within the fluidics unit. On the other hand, the module, which contains the fluidics unit, can therewith be produced economically, especially as a single-use component. In the case of a reconditioning of the above described cassette, it can then be economically sensible not as above described to recondition the first module containing the fluidics unit, but, instead, to dispose of it after use.

The first and/or the second module can include a heating apparatus, especially a controllable thermoelectric element, for example, a Peltier element, or a controllable heating element and a temperature sensor. The heating apparatus can be used to hold the reagents and the liquid sample at a constant temperature. This can be assured by the control unit of the system based on the measured values delivered by the temperature sensor. Heating apparatuses can also be arranged, with targeting, for example, in the region of a functional unit the fluidics unit, in order to set a certain temperature locally.

For example, an option is to perform in a functional unit a chemical reaction, which can be accelerated by increasing the reaction temperature. In this case, there can be arranged in the region of the functional unit a heating element, which locally increases the temperature of the reaction mixture present in the functional unit.

The system for treating liquids can furthermore comprise a signal registering- and/or signal producing system, which is embodied to register a property, especially an optical or magnetic property, of an analyte, or a reaction product of the analyte, present in the at least one functional unit of the fluidics unit. The signal registering system can be, for example, an optical apparatus with a radiation source, especially an LED, and a photodetector, especially a photodiode, in order to register absorption- or fluorescent properties of the analyte or the reaction product and to win therefrom quantitative information concerning the concentration of the analyte in the sample liquid. The first module can especially have a beam path transparent for radiation emitted by the radiation source, wherein the beam path passes through at least one part of the functional unit, in order to register an optical property of the analyte or of a reaction product of the analyte.

BRIEF DESCRIPTION OF THE DRAWINGS

The invention will now be described in detail based on the examples of embodiments shown in the drawing, the figures of the which show as follows:

FIG. 6 a) an embodiment of the pneumatic interface and the liquid storage unit in the separated state;

FIG. 6 b) the pneumatic interface the FIG. 6 a) in the connected state;

FIG. 8 b) a pneumatically actuatable valve in the open state;

FIG. 9 b) the pneumatically actuatable, normally closed, pinch valve in the open state;

FIG. 10 b) the pneumatically actuatable, normally open, pinch valve in the closed state;

FIG. 13 b) a liquid storage unit with a therein arranged, flexible, liquid container in a second embodiment in the filled state; and FIG. 13 c) a liquid storage unit with a therein arranged, flexible, liquid container in the second embodiment in the almost empty state.

DETAILED DISCUSSION IN CONJUNCTION WITH THE DRAWINGS

Figure 1:
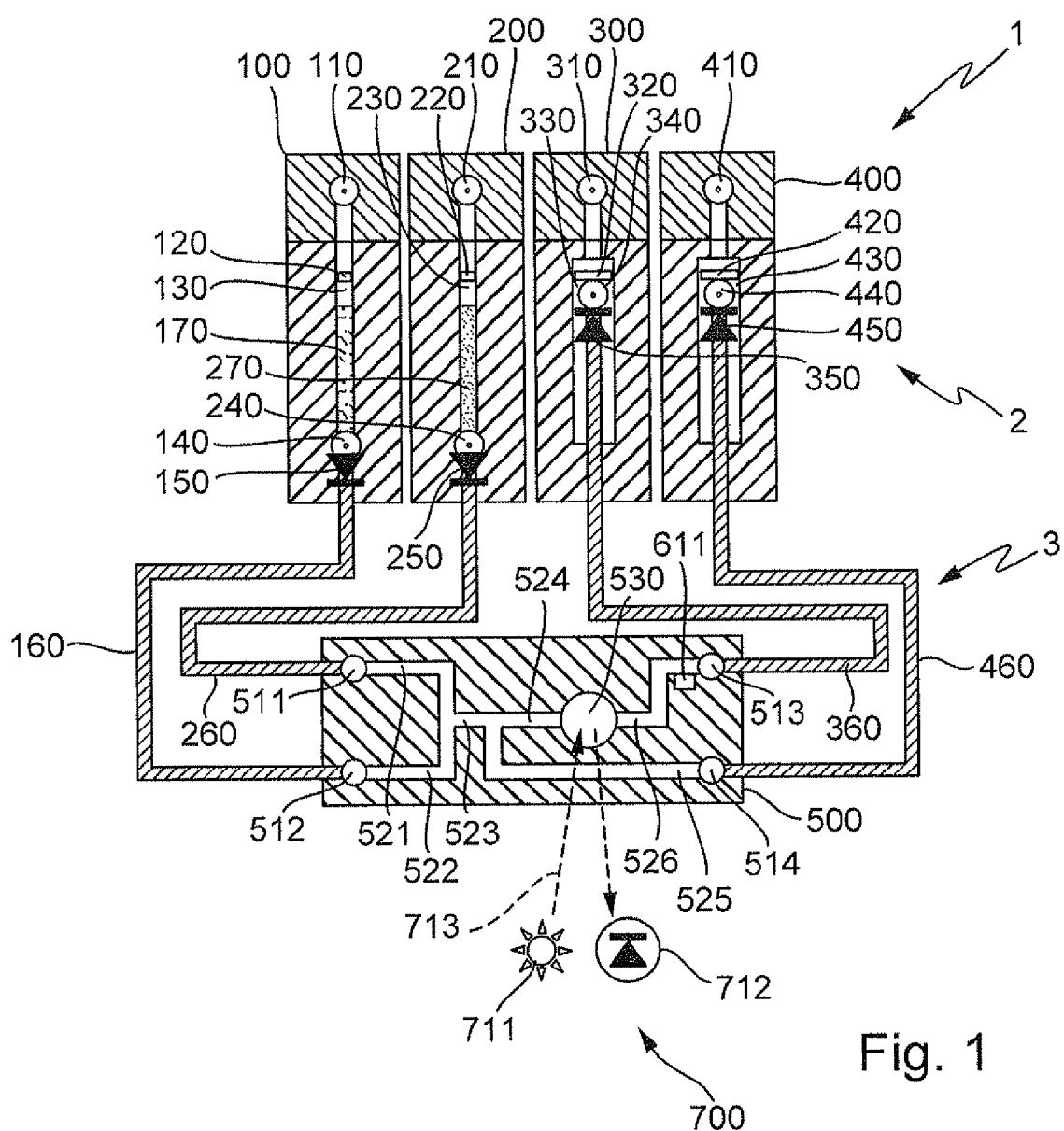
FIG. 1 a schematic representation of a system for treating liquids.

FIG. 1 shows a schematic representation of a system 1 for treating liquids, which can be used, for example, in an analytical system. System 1 includes, in the example shown in FIG. 1, four liquid cartridges, namely a first supply cartridge 100 and a second supply cartridge 200, as well as a first waste cartridge 300 and a second waste cartridge 400. The two supply cartridges 100, 200 contain supply storage units 130 and 230, which serve as liquid storage units of the first type. The two waste cartridges 300 and 400 contain waste storage units 330 and 430, which serve as liquid storage units of the second type. Furthermore, system 1 includes a fluidics unit 500 and liquid supply lines 160 and 260, which connect the supply storage units 130 and 230 with the fluidics unit 500, as well as liquid drain lines 360 and 460, which connect the fluidics unit 500 with the waste storage units 330 and 430. The supply storage units 130, 230 contain liquids 170, 270, which can be led via the liquid supply lines 160, 260 connected to the supply storage units 130, 230 into the fluidics unit 500. The two waste storage units 330 and 430 are embodied to receive consumed liquids 170, 270 and mixtures of these liquids 170, 270, which are supplied to them from the fluidics unit 500 via the liquid drain lines 360, 460. The supply cartridges 100, 200 and the waste cartridges 300, 400 can be connected durably with one another, and, in given cases, be surrounded by a housing, so that they form an integrated module 2.

The supply cartridges 100, 200 and the waste cartridges 300, 400 have connections 110, 210, 310, 410 for the connection of the respective liquid storage unit 130, 230, 330, 430 contained in the liquid cartridge to a pneumatic line of a pneumatic system (not shown in FIG. 1). The connections 110, 210, 310 and 410 thus form a pneumatic interface of the system 1.

The supply storage units 130 and 230 in the supply cartridges 100 and 200 are embodied, for example, as bores within the cartridges. The supply storage units 130, 230 can accommodate, for example, reagents, regenerating liquid for regeneration e.g. of functional units of the fluidics unit 500 or cleaning liquid for cleaning the fluidics unit 500. A supply storage units can also serve as a buffer for the sample to be analyzed, which, first of all, is removed, preferably automatically, for example, by means of a peristaltic pump or a syringe pump or by means of a pneumatic sample taking apparatus with pneumatic sample transport, from a process vessel, for example, a pipeline of a process installation, and, thereafter, filled into the supply storage units.

The supply cartridges 100 and 200 include, in each case, a connection 140, 240 for connecting the supply storage units 130, 230 to the fluidics system 500. The connections 140, 240 can, in each case, be coupled to a liquid supply line 160, 260 of the fluidics system 500, so that a fluid connection between the supply storage units 130, 230 and the fluidics unit 500 is formed. Correspondingly, the waste cartridges 300 and 400 include, in each case, a connection 340, 440 for connecting the waste storage units 340, 440 to the fluidics system 500. The connections 340, 440 can, in each case, be coupled to a liquid discharge line 360, 460 of the fluidics system 500, so that a fluid connection between the fluidics unit and the waste storage units 330, 430 is formed. In this way, the supply storage units 130, 230 and the waste storage units 330, 430 are fluidically connected for forming, in each case, at least one flow path leading through the fluidics unit 500 from a supply storage unit to a waste storage unit. A fluidic connection means here and in the following a structural connection between two components, here e.g. between a liquid storage unit and the fluidics system 500, especially the liquid lines and functional elements present in the fluidics system 500, via which a fluid, preferably a liquid, can be transferred from the first to the second component. Especially, it is not excluded that additional components are arranged between the first and second components standing in fluid connection. A fluid connection is furthermore especially sealed in such a manner that a loss free transfer of the fluid between the first and second components is possible.

In the region of the connections 140, 240 of the supply storage units 130, 230 is arranged, especially as a component of the module 2 formed by the cartridges 100, 200, 300 and 400 with the liquid storage unit 130, 230, 330, 430, in each case, a first check valve 150, respectively a second check valve 250, blocking in the direction from the fluid unit 500 toward the first supply storage unit 130, respectively the second supply storage unit 230. These, thus, block flow of liquid and, in given cases, gas from the fluidics unit 500 back into the supply storage units 130, 230. The first check valve 150 and the second check valve 250 are preferably so embodied that they only allow liquid to flow in the pass through direction, thus from the supply storage units 130, 230 to the fluidics unit 500, after the reaching of a certain minimum pressure, the so-called breakthrough pressure or opening pressure. In such case, the opening pressure is so selected that the hydrostatic pressure of the reagents 170, 270 in the supply storage units 130, 230 in the completely filled state acting on the check valves 150, 250 alone is not sufficient to exceed the opening pressure.

Arranged in the region of the connections 340 and 440 of the waste storage units 330, 430, especially as a component of the module 2, is, in each case, a third check valve 350, respectively a fourth check valve 450, which blocks flow from the waste storage units 330 and 430 to the fluidics unit 500. Check valves 330, 430, thus, block flow of liquid and, in given cases, gas from the waste storage units 330, 430 back into the liquid drain lines 360, 460 and, thus, into the fluidics unit 500. Check valves 350 and 450 are so designed that a certain opening pressure is required, in order to permit flow of liquid in the pass through direction. The opening pressure of the third check valve 350, respectively the fourth check valve 450, can, in such case, be selected somewhat smaller than the opening pressure of the first check valve 150, respectively the second check valve 250.

The connections 140, 240, 340 and 440 of all liquid storage units, i.e. the supply storage units 130, 230 and the waste storage units 330, 430, form an interface of the cartridges module 2 for connecting the fluidics unit 500 to the liquid storage unit. This interface is also referred to as the fluidics interface.

All supply cartridges 100, 200 and all waste cartridges 300, 400 have, between their liquid storage unit 130, 230, 330, 430 and the associated connection 110, 210, 310 and 410 for connecting the pneumatic system, a closure element 120, 220, 320 and 420, for example, a diaphragm, a membrane or a filter, which is, indeed, gas permeable, yet impermeable for liquids. This prevents that liquid can escape from the liquid storage unit 130, 230, 330 and 430 into the pneumatic lines, or, in case no pneumatic lines are connected to the pneumatic interface of the cartridges, into the environment. For biochemical or sterile applications of system 1, the gas permeable fasteners 120, 220, 320 and 420 can be so embodied that no microorganisms can penetrate into the liquid storage units, respectively that no microorganisms can escape from the liquid storage units.

Liquid present within the supply storage units 130, 230 and the waste storage units 330, 430 can be contained in flexible, gaseous- and liquid impermeable containments, which are connected to the respective liquid lines 160, 260, 360, 460 connecting the liquid storage units 130, 230, 330, 430 with the fluidics unit 500. These flexible containments can be, for example, bags made of a flexible material (such as, for example, a plastics film). The bags sit in the respective liquid storage units 130, 230, 330, 430. This will be described below in connection with FIG. 9.

A supply storage unit, which serves as buffer for the sample liquid, includes an additional connection for delivery of sample liquid (not shown). Correspondingly, then also the flexible containment arranged within the liquid storage unit includes a connection for introducing the sample. These connections can be sealed to the environment by means of a valve, e.g. a check valve, so that no sample liquid escapes upon removal of the module 2, which includes the liquid cartridge serving as buffer for the sample.

Fluidics unit 500 includes a treating cartridge, in which liquids can be successively passed through, mixed, chemically converted, heated, analyzed or otherwise handled in some other manner. When system 1 is a microfluidics-system, the treating cartridge is embodied in the form of a microfluidics unit, especially a microfluidics chip. The treating cartridge includes a series of liquid lines 521, 522, 523, 524, 525, which are connected via connections 511, 512, 513, 514 fluidically with the liquid supply lines 160, 260 coming from the supply cartridges 100, 200 and the liquid drain lines 360, 460 leading to the waste cartridges 300, 400. The treating cartridge can be formed, for example, from a substrate, whose surface has channels forming the liquid lines, and a cover plate bearing on this surface. The material for the treating cartridge can be, for example, silicon, synthetic material, such as plastic, or glass. When the treating cartridge is embodied as a microfluidics chip, the liquid lines 521, 522, 523, 524, 525 are embodied as capillary channels in a silicon substrate. For manufacture of such a microfluidics chip, materials and manufacturing processes known from the state of the art, especially from the field of "lab on a chip" technology, can be used. In an alternative embodiment, the liquid supply lines 160, 260 and the liquid drain lines 360, 460 can be omitted by directly connecting the connections of the treating cartridge with the fluidics connections 140, 240, 340, 440 of the liquid cartridges 100, 200, 300, 400. This can be implemented, for example, by providing detents in the connections of the treating cartridge and the fluidics connections 140, 240, 340, 440 of the liquid cartridges 100, 200, 300, 400. The detents are brought into sealing engagement with one another, in order to establish a fluid transporting connection.

In the example of FIG. 1, the liquid cartridges are accommodated in a single replaceable module 2, which is embodied, for example, as a cassette. The fluidics connections 140, 240, 340, 440 of the module 2 can be equipped with detents, which can be connected with detents of connections of a module 3 by bringing the detents into fluid-tight engagement. Module 3 is embodied, for example, likewise as a cassette, which includes the fluidics unit 500 and the liquid lines 160, 260, 360 and 460. Preferably, the replaceable module 2 includes guiding means, which interact with complementary guiding means of the replaceable module 3 in such a manner that the module 3 can be connected only in a predetermined orientation relative to that of the replaceable module 2. In this way, it is assured that the supply storage units 130, 230 and the waste storage units 330, 430 are connected to the liquid lines 160, 260, 360, 460 of the fluidics unit 500 respectively provided for them.

In the example shown here, the fluidics unit 500 has a system of liquid lines 521, 522, 523, 524, 525 suitable to supply two liquids 170, 270 from the two supply storage units 130, 230 one after the other to the functional unit 530, in order to perform there a photometric measurement, for example. For this, it includes a first liquid line 522 connected via its connection 512 with the first supply storage unit 130 and a second liquid line 521 connected with the second supply storage units 230 via the connection 511, wherein the first and second liquid lines 521, 522 combine at a first point to a third liquid line 523, which branched at a second point remote from the first point into a fourth liquid line 524 and a fifth liquid line 525. The fourth liquid line 524 opens into the functional unit 530, while the fifth liquid line 525 leads to the second waste storage unit 430, with which it is connected via the connection 514. Leading away from the functional unit 530 is a sixth liquid line 526, which is fluidically connected with the first waste storage unit 330 via the connection 513.

In the present example, the functional unit 530 is formed by a chamber, which has a circularly shaped base. The chamber has an inlet formed by the channel section 523 and an outlet formed by the liquid line 524. The functional unit can in another example also be embodied as a meander or in other manner known from "lab on a chip" technology. Applied on the base of the functional unit 530 can be, for example, a layer of biochemical receptors, to which a biomolecule to be detected specifically binds. A liquid sample, which contains the analyte to be determined, can be brought, for example, from one of the supply storage units 130, 230, via the liquid line 523 into the functional unit 530. Analyte contained in the sample is there specifically bound to the receptors applied on the base of the functional unit 530. The amount of the analyte molecules bound to the receptors can be determined, for example, by means of an optical measurement. For optical detection of the analyte, system 1 includes an optical signal registering system 700, which comprises a light source 711, for example, a light emitting diode (LED), and a receiver 712, for example, a photodiode. In support of this, the fluidics unit 500 is transparent at least along a beam path 713 for the radiation of the light source 711 extending from the light source 711 through the functional unit 530 to the photodetector 712. For this, can, for example, the fluidics unit 500 be manufactured of a material transparent for the measuring wavelength of the signal registering system 700, or at least have a window of such material. Alternatively, the radiation of the light source 711 can also be led by optical fibers to the functional unit 530 and likewise brought via light conductors from the functional unit 530 to the photodetector 712.

Arranged in the sixth liquid line 526 is a sensor 611, which is a flow measuring transducer in the present example. The flow measuring transducer is connected with a control unit (not shown in FIG. 1) of system 1. Based on a measured value currently delivered by the flow measuring transducer 611, the control unit can control the pneumatic unit to assure a uniform flow through the fluidics unit 500. Of course, the same type of flow measuring transducer can also be arranged in one or more additional liquid lines 521, 522, 523, 524 and 525. Suitable flow measuring transducers for such microfluidic applications are described, for example, in US 2009/0126505 A1 or in WO 2007/147786 A1 or U.S. Pat. No. 6,477,901 A. The flow measuring transducers in the two latter documents are Coriolis flow measuring devices in MEMS technology. Sensor 611 can alternatively also be a temperature- or conductivity sensor. Also a number of such sensors 611 can be provided within the fluidics unit 500, in order to register different measured variables of liquids the flowing through the treating cartridge.

System 1 includes supplementally to the module 3 with the fluidics unit 500 and the liquid lines 160, 260, 360, 460 and the module 2, which includes the liquid storage units 130, 230, 330, 430, the already mentioned control unit, which is furthermore embodied for evaluation of data of the optical signal registering unit 700, for evaluation of data of additional sensors 611, as well as for display of information and analytical results. Furthermore, system 1 includes the already mentioned pneumatic system, which serves for the transport of liquids from the supply storage units 130, 230 into the waste storage units 330, 430 through the fluidics unit 500. While the liquid storage units 130, 230, 330, 430 and the fluidics unit 500 as described can, be integrated in replaceable modules, the control unit and the pneumatic system are preferably fixed components of system 1 and can be durably integrated, for example, in a housing structure, into which the replaceable modules 2, 3 are insertable.

Based on FIGS. 2 to 5, the liquid transport within the treating unit 501 with the assistance of the pneumatic unit will now be described. In the example shown here, all channels are initially filled with liquid.

Figure 2:
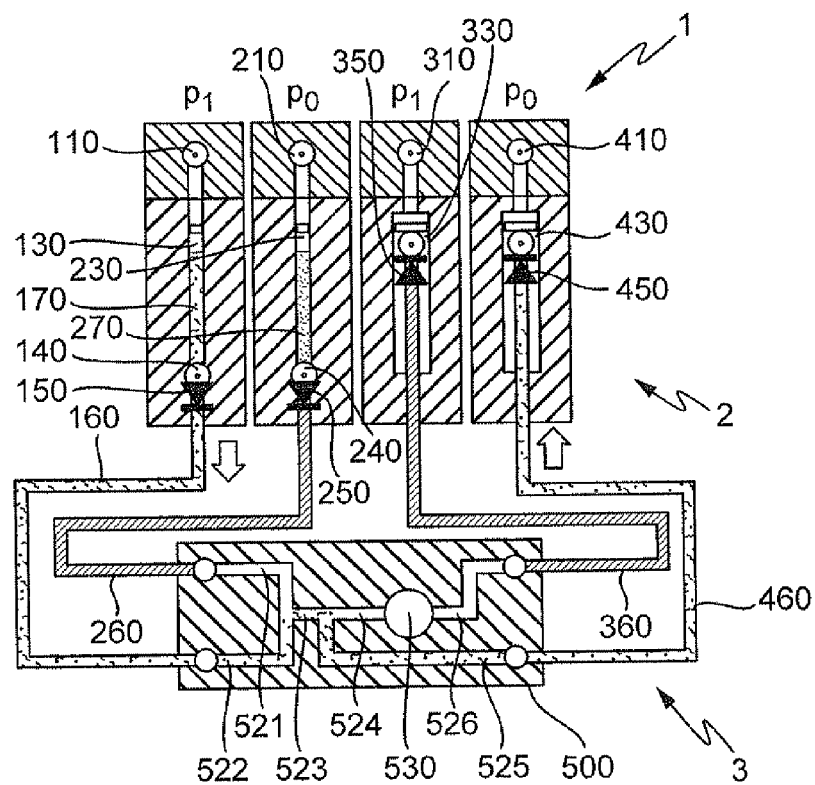
FIG. 2 the system of FIG. 1 during a first treating step.

In a first step illustrated in FIG. 2, a first liquid 170, e.g. a liquid sample, is brought from the first supply storage units 130 into the fluidics unit 500. For this, the pneumatic unit (not shown), which is connected via the pneumatic interface (comprising the connections 110, 210, 310 and 410) with the supply storage units 130, 230, 330 and 430, applies to the first supply storage unit 130 a first pressure P1 and to the second waste storage units 430 a gas pressure P0, which is less than the first pressure P1. In this way, there arises a pressure difference P1-P0 between the first supply storage units 130 and the second waste storage unit 430. If the sum of this pressure difference and the hydrostatic pressure of the first reagent 170 in the first supply storage units 130 exceeds the sum of the breakthrough pressure of the first check valve 150, the breakthrough pressure of the fourth check valve 450 and the resistance of the affected liquid lines, the first liquid 170 is led via the first check valve 150 in the pass through direction into the liquid supply line 160 to the fluidics unit 500 and via the connection 512 into the second liquid line 522 of the fluidics unit 500. The second check valve 250 blocks fluid transport into the second supply storage unit 230, to which during the treating step illustrated in FIG. 2 a pressure P0 is applied, which equals the pressure P0 applied to the second waste storage unit 430. Applied to the first waste storage unit 330 is a pressure P1, which equals the pressure P1 applied to the first supply storage unit. Therewith, there is no pressure difference between the second supply storage unit 230 and the second waste storage unit 430, so that the breakthrough pressure of the second check valve 250 is not overcome, and so no liquid transport takes place between the second supply storage unit 230 and the second waste storage unit 430. A transport of the first liquid 170 introduced into the fluidics unit 500 toward the second supply storage units 230 is suppressed by the second check valve 250, which blocks all fluid transport from the fluidics unit 500 to the second supply storage unit 230. Since there is applied to the first waste storage unit 330 the same pressure P1 applied also to the first supply storage units 130, the first reagent 170 is led further through the third liquid line 523 and the fourth liquid line 525 via the connection 514, the liquid line 460 and the fourth check valve 450 into the second waste storage unit 430.

Figure 3:
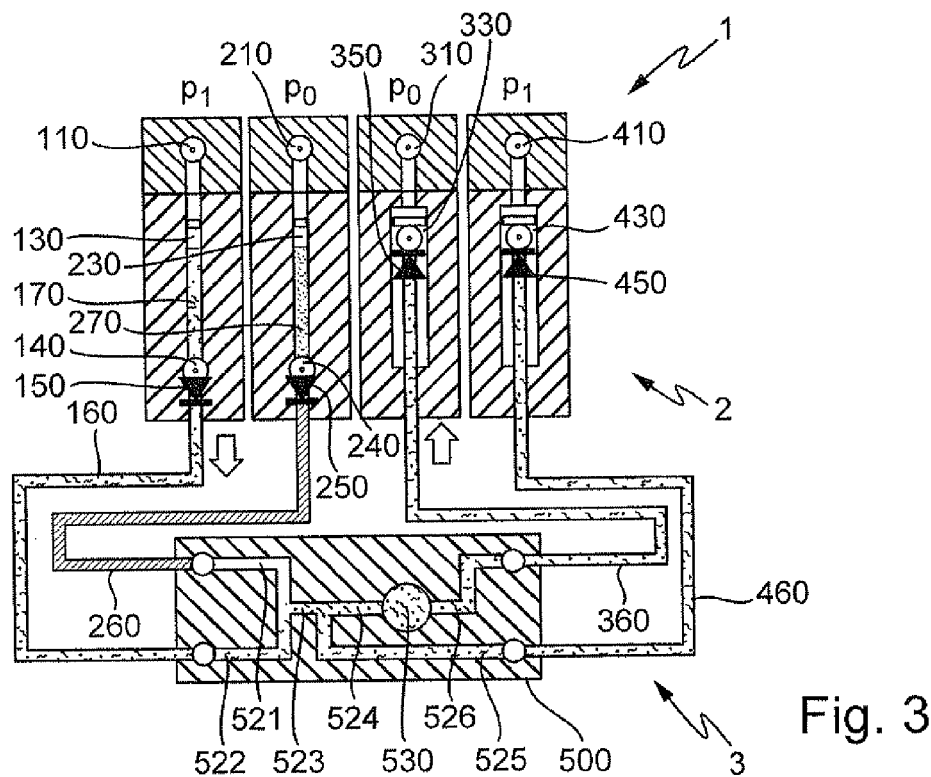
FIG. 3 the system of FIG. 1 during a second treating step.

FIG. 3 shows a second method step, in the case of which the pneumatic unit applies the same pressure P1 to the first supply storage unit 130 and to the second waste storage unit 230, and to the second supply storage unit 230 and the first waste storage unit 330, in each case, the same pressure P0, which is lower than P1. Therewith, there results between the first supply storage unit 130 and the second waste storage unit 330 a pressure difference P1-P0, which, in case the sum of the pressure difference P1-P0 and the hydrostatic pressure exerted by the first liquid 170 in the first supply storage units 130 on the check valve 150 is greater than the sum of the breakthrough pressure of the first check valve 150, the breakthrough pressure of the third check valve 350 and the resistance of the liquid lines, leads to a liquid transport of the first liquid 170 from the supply storage unit 130 to the first waste storage unit 330. In such case, the flow path of the first liquid 170 leads via the first check valve 150, the liquid supply line 160, the connection 512, the second liquid line 522, the third liquid line 523, the fourth liquid line 524, the functional unit 530, the sixth liquid line 526, and the liquid discharge line 360 into the first waste storage unit 330. On the branching point, at which the third liquid line 523 branches into the fourth liquid line 524 and the fifth liquid line 525, the first liquid 170 is led in the direction of the functional unit 530, since there is applied to the fifth liquid line 525 via the second waste storage unit 430 an increased pressure P1.

Based on FIG. 2 and FIG. 3, it is, thus, recognizable that, through corresponding choice of the pressures applied to the supply storage units 130, 230 and the waste storage units 330, 430 via the pneumatic interface, a liquid at a branching within the fluidics unit 500 can take the first or the second branch path, without a valve or some other actuatable element being required therefor in the fluidics unit 500.

Figure 4:
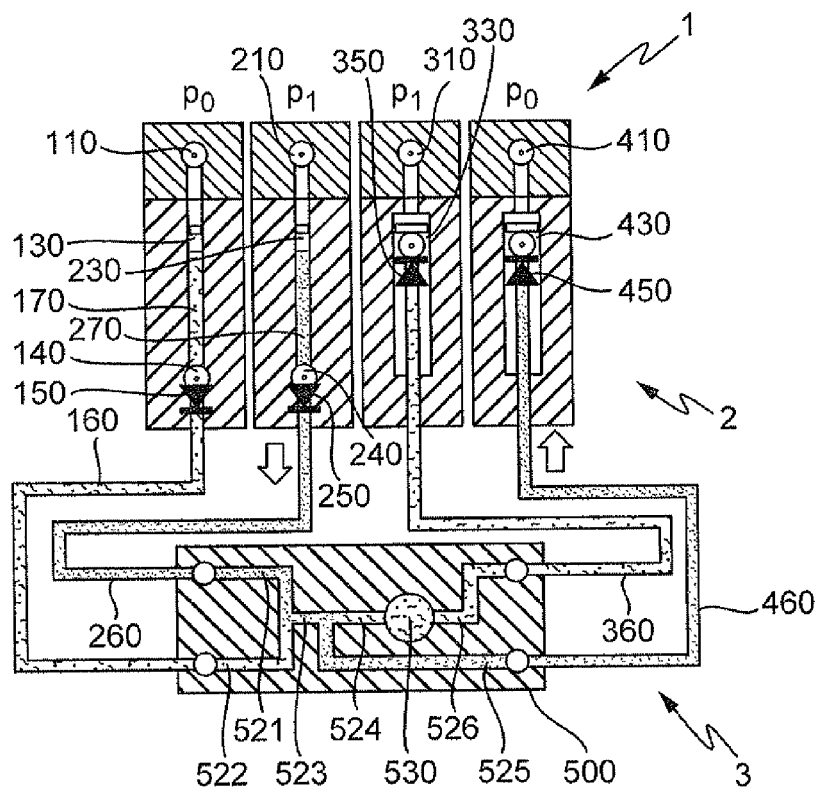
FIG. 4 the system of FIG. 1 during a third treating step.

FIG. 4 shows an additional method step, in the case of which a first pressure P0 is applied to the first supply storage unit 130 and the second waste storage unit 430, and a higher pressure P1 to the second supply storage unit 230 and the first waste storage unit 330. In this way, a pressure difference P1-P0 results between the second supply storage unit 230 and the second waste storage unit 430. If is the sum of this pressure difference and the hydrostatic pressure of the second liquid 270 present in the second supply storage unit 230 is greater than the sum of the breakthrough pressure of the second check valve 250, that of the fourth check valve 450 and the resistance of the liquid lines, then the second liquid 270 can flow from the second supply storage unit 230, through the check valve in the direction of the fluid line 260, and via the connection 511 into the fluidics unit 500. Between the first waste storage unit 330 and the first supply storage unit 130, there is likewise a pressure difference P1-P0. A back flow of liquid from the first waste storage unit 330 is, however, prevented by the blocking action of the check valve 350 sealing such. Also, a flowing of liquid back from the fluidics unit 500 via the line 160 to the first supply storage units 130 is prevented by means of the first check valve 150 blocking flow in such direction. The second liquid 270 can also not take the flow path via the fourth liquid line 524 into the functional unit 530, since the same pressure P1 is applied to the first waste storage unit 330 as to the second supply storage unit 230.

Figure 5:
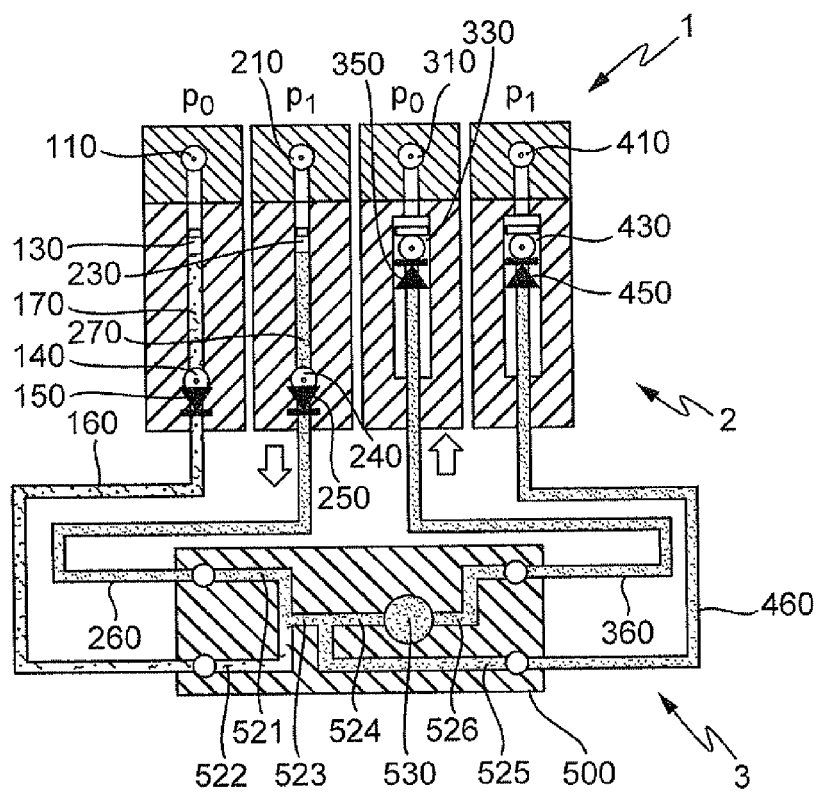
FIG. 5 the system of FIG. 1 during a fourth treating step.

FIG. 5 shows a fourth method step. In such case, there is applied to the second supply storage unit 230 a pressure P1 and to the first waste storage unit 330 a lower, second pressure P0. Applied to the first supply storage unit 130 is likewise the lower pressure P0, while to the fourth waste storage unit 430 the higher pressure P1 is applied. Due to the pressure difference P1-P0, which exists between the second supply storage unit 230 and the first waste storage unit 330, the second liquid 270 can, to the extent that the pressure difference P1-P0 together with the hydrostatic pressure of the second liquid 270 in the supply storage unit 230 exceeds the breakthrough pressure of the second check valve 250, the breakthrough pressure of the third check valve 350 and the resistance of the liquid lines, flow from the second supply storage unit 230 through the fluidics unit 500 to the first waste storage unit 330. In such case, the second liquid 270 flows via the first liquid line 521 and the third liquid line 523 into the functional unit 530. At the branching point, where the third liquid line 523 branches into the fourth liquid line 524 and the fifth liquid line 525, the second liquid 270 cannot divert into the fifth liquid line 525, since the same pressure P1 is applied to the second waste storage unit 430 as to the second supply storage unit 230.

The connections 110, 210, 310 and 410 for connecting the liquid cartridges 100, 200, 300 and 400 to a pneumatic system are components the liquid cartridges 100, 200, 300 and 400 in the example shown in FIGS. 1 to 5. Alternatively, the supply storage units 130, 230 with the waste storage units 330 and 430 and the associated pneumatic connections 110, 210, 310 and 410 can be arranged in separate, i.e. separable from one another, components. In this case, for example, all liquid storage units can be combined in a shared, replaceable module, especially in a shared housing, e.g. in the form of a cassette, while the connections 110, 210, 310, 410 are combined in an additional module, especially likewise in a shared housing. The two modules can be connected releasably with one another via one or more pneumatic interfaces, as shown in FIG. 6. Advantageously, the other module is integrated durably in a housing structure of system 1 and connected permanently with the pneumatic system.

FIG. 6 a) shows, schematically, an example of an embodiment, in the case of which the liquid storage units 130, 230, 330, 430 are combined in a liquid storage unit module 800 with a pneumatic interface, which includes the connections 180, 280, 380, 480. The pneumatic connections 110, 210, 310 and 410 connectable to a pneumatic system (not shown) are accommodated in a connector module 801, which can be connected releasably with the liquid storage unit module 800 via connections 181, 281, 381, 481 complementary to the connections 180, 280, 380, 480 of the liquid storage unit module 800. In the separated state, the escape of liquid from the supply storage units 130, 230, and the waste storage units 330 and 430 into the environment is prevented by the gas permeable, however, liquid tight, closure elements 120, 220, 320 and 420. In the connected state of the two modules (FIG. 6 b), the system can be operated in the manner shown in FIGS. 2 to 5.

The liquid storage unit module 800 includes furthermore connections 140, 240, 340, 440 for the liquid supply lines 160, 260 and the liquid drain lines 360 and 460. These connect the supply- and waste cartridges with the fluidics unit 500. Fluidics unit 500 and the liquid lines 160, 260, 360 and 460 can also be embodied combined in a replaceable module (s. module 3, FIG. 1), especially in a housing releasably connectable with the liquid storage unit module 800, e.g. in the form of a cassette. In such case, it is advantageous to provide the liquid lines 160, 260, 360 and 460 with connections, which are so arranged that they fit directly with the complementary fluidics connections 140, 240, 340, 440 of the liquid storage unit module 800, so that the two modules need only be plugged in to one another, in order to connect the liquid supply lines 160, 260 to the fluidics unit 500 and the liquid drain lines 360 and 460 from the fluidics unit to the waste cartridges 300, 400 with the fluidics connections 140, 240, 340, 440 of the liquid storage unit module 800.

Figure 7:
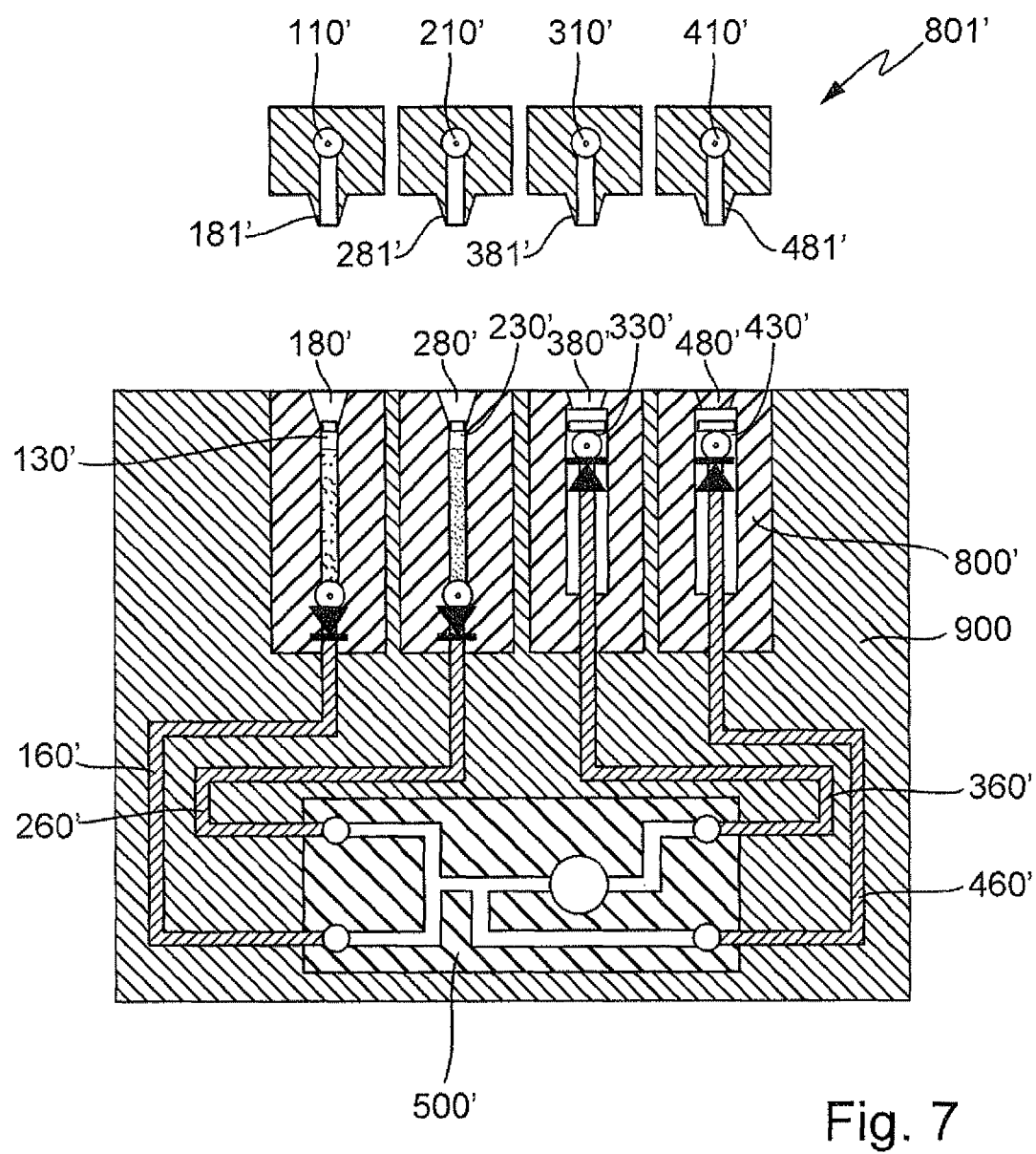
FIG. 7 for connection releasably with the pneumatic system via the pneumatic interface, a cassette, which includes liquid storage units and a fluidics unit.

FIG. 7 shows schematically a further example of an embodiment. In such case, the earlier described liquid storage unit module 800' with the supply storage units 130', 230' and the waste storage units 330', 430', the fluidics unit 500', the liquid supply lines 160', 260' between the supply storage units 130', 230' and the fluidics unit 500' and the liquid drain lines 360', 460' between the fluidics unit 500' and the waste storage units 330', 430' are combined in a housing unit sealed to the environment, i.e. surrounded by a sealed housing, in the following referred to as cassette 900. The connections of the cassette are formed by a sample supply line (not shown) to one of the supply storage units 130', 230' and by a pneumatic interface, which has pneumatic connections 180', 280', 380', 480', which can be connected releasably with complementary connections 181', 281', 381', 481' of an additional module 801', which includes other connections 110', 210', 310', 410' for connecting to a pneumatic unit. Therewith, the cassette 900 can be separated as a replaceable module of a system for treating liquids, e.g. an analytical system, same as a printer cartridge for an ink jet printer, as a whole, from the pneumatic unit and replaced by another cassette, especially an equally constructed cassette. This can occur especially when maintenance measures are necessary, e.g. when one of the supply storage units 130' or 230' is completely empty or when one of the waste storage units 330' and 430' is completely filled and can accommodate no more liquid. An operator, thus, does not have to replace the individual liquid storage units, but, instead, need only disconnect the cassette 900 at the interfaces 180', 280', 380', 480' and, thus, separate it from the system 1', and replace it with a new, same type, especially equally constructed, cassette. This has the advantage that the operator does not have to have accumulated a lot of knowhow, in order to maintain the system 1'. To assure that the cassette 900 can be connected to the connections 181', 81', 381', 481' of the other module 801' in only one possible orientation, the two modules can have guiding means complementary to one another, which engage, and so enable the connecting of their complementary connections, only in the case of a predetermined orientation of the two modules relative to one another. A reconditioning of the cassette 900, for example, a renewed filling of the liquid storage units with reagents can be performed, for example, at the plant of the manufacturer.

Figure 8A:
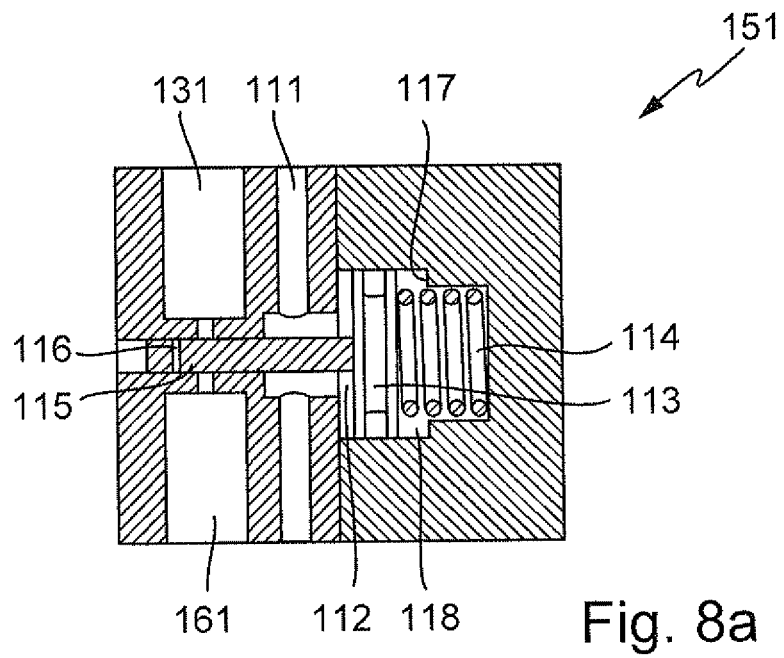
FIG. 8 a) a pneumatically actuatable valve in the closed state.
Figure 8B:
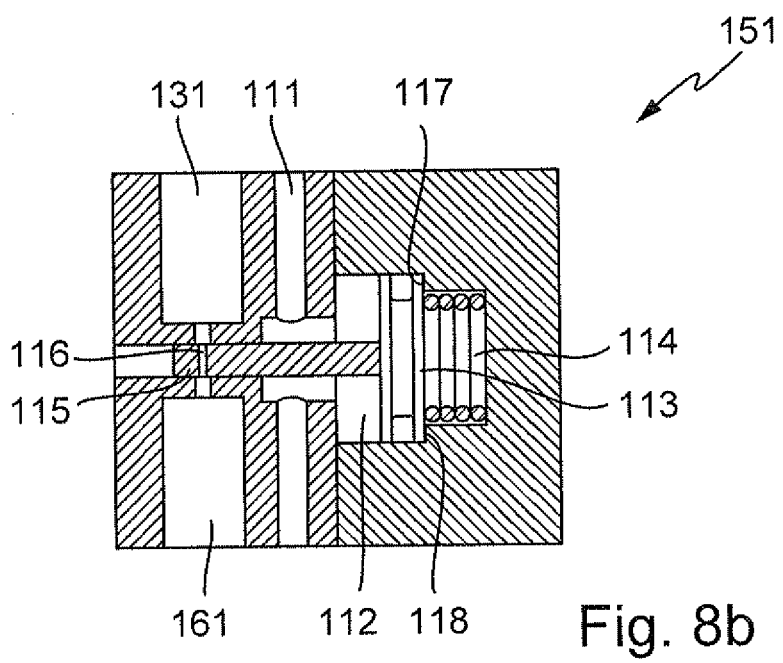

In the examples of embodiments illustrated in FIGS. 1 to 7, for blocking flow of liquid 170, 270 through the liquid supply lines 160, 260 from the fluidics unit 500 to the supply storers 130, 230, or for blocking the flow of liquid 170, 270 through the liquid drains 360, 460 from the waste storage units 330, 430 to the fluidics unit 500, in each case, check valves 150, 250, 350, 450 are provided. Alternatively, instead of the check valves 150, 250, 350, 450, pneumatically actuated valves can be provided. These can be embodied in many different ways. FIGS. 8 *a*) and *b*) show an example of a pneumatically actuatable valve 151, which is a normally closed valve. Valve 151 can be arranged in such a manner between a liquid storage unit, e.g. a supply storage unit 130, 230, and a liquid line, e.g. a liquid supply line 160, 260, to the fluidics unit 500 that a first interface 131 facing the liquid storage unit is in fluid connection with the liquid storage unit 130, 230 and so liquid can move from the liquid storage unit to the interface 131. Equally, a second interface 161 facing away from the liquid storage unit is in fluid connection with the liquid line, so that liquid can move from the interface 161 into the liquid line. The first interface 131 is in the closed, rest position of the valve 151 illustrated in FIG. 8 *a*) liquid sealed from the second interface 161 by a closure element 115, so that no liquid can get from the liquid storage unit connected with the first interface 131 into the liquid line connected with the second interface 161.

Connected with the closure element 115 is a piston 113, which is arranged movably in a hollow space formed in the valve housing in such a manner that it divides the hollow space into a first valve space 112 and a second valve space 118. The first valve space 112 is connected with a pressure line 111, via which the first valve space 112 can be supplied with a pressurizing medium, for example, compressed air. Putting pressure into the first valve space 112 effects a force on the movable piston 113, and this leads to a shifting of the piston 113 in the direction of the second valve space 118. Arranged in the second valve space 118 is a return spring 114, which exerts a return force on the piston 113. In the rest position of the valve 151 illustrated in FIG. 8 *a*), pressure line 111 carries atmospheric pressure and the return spring 114 is not compressed.

In FIG. 8 *b*), valve 151 is shown in its opened state, in which a pressure is applied in the pressure line 111 via a pressurizing medium, e.g. compressed air. The applied pressure is so dimensioned that the force exerted on the piston 113 overcomes the return force of the spring 114 and so effects a shifting of the piston 113 counter to the return force of the spring 114, wherein the shifting movement of the piston 113 is limited by a stop 117. With the shifting of the piston 113 toward the second valve space 118, there occurs simultaneously a shifting of the closure element 115 with connected the piston 113, whereupon a fluid connection between the first interface 131 and the second interface 161 is formed. This connection is formed in the present example by means of a passageway 116 of the closure element 115, which aligns with openings of the first interface 131 and the second interface 161, when the piston 113 contacts the stop 117. Via this fluid connection, liquid from the liquid storage unit connected with the first interface 131 can move into the liquid line connected with the second interface 161, or in the reverse direction from the liquid line into the liquid storage unit.

Figure 9A:
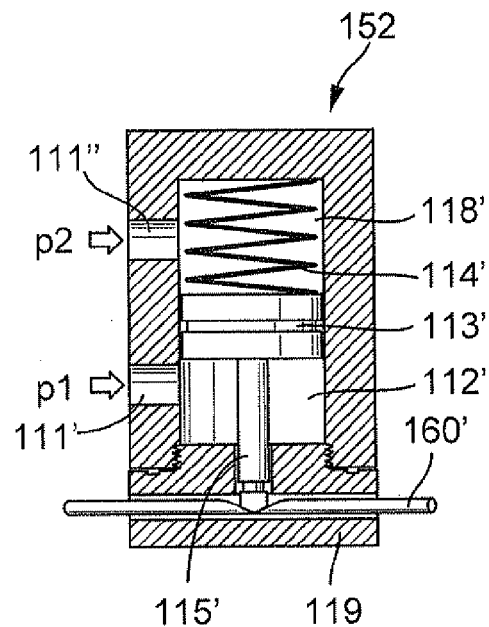
FIG. 9 a) a pneumatically actuatable, normally closed, pinch valve in the closed state.
Figure 9B:
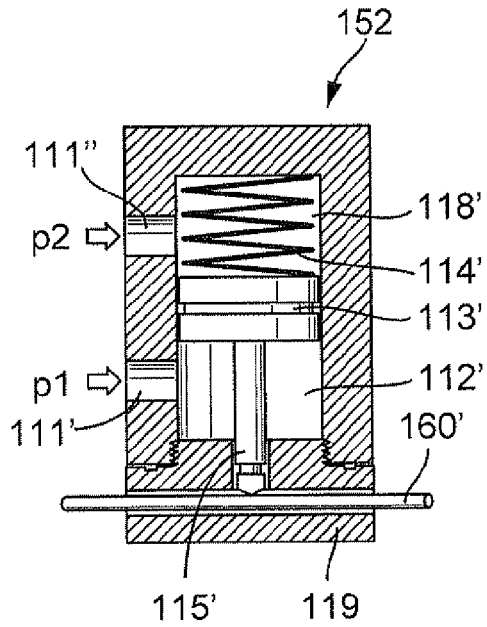

FIGS. 9 *a*) and *b*) shows a pneumatically actuatable, normally closed, pinch valve 152. Such pinch valves can be applied in an embodiment of the system 1 for treating of liquids, in which liquid supply lines 160, 260 of the supply storage units 130, 230 to the fluidics unit 500, or liquid drain lines 360, 460 from the fluidics unit 500 to the waste storage units 330, 430 are embodied, at least sectionally, with a flexible wall, such as is the situation, for example, in the case of hoses. Valve 152 can be arranged in such a manner between a liquid storage unit, e.g. a supply storage unit 130, 230 and the fluidics unit 500 that it acts on the liquid line 160, 260 connecting the liquid storage unit and the fluidics unit 500, in order, at least at times, to block liquid transport through these liquid line 160, 260.

The pinch valve 152 is embodied similarly to the pneumatically actuated valve 151 shown in FIG. 8. Pinch valve 152 includes a housing, in which a preferably cylindrical, hollow space is formed, which is divided by a movable piston 113' into a first valve space 112' and a second valve space 118', wherein the piston 113' rests gas tightly on the wall of the hollow space. The first valve space 112' is connected with a first pneumatic line 111', via which the first valve space can be supplied with a pressurizing medium, for example, compressed air. The pressurizing medium is supplied by a pneumatic system, which is connected with the pinch valve 152 via the only schematically indicated pneumatic line 111'. A first pressure p1 can be applied to the first valve space 112' through the pneumatic line 111'. This pressure in the first valve space 112' effects a force on the movable piston 113', which leads to a shifting of the piston 113' in the direction of the second valve space 118'. Arranged in the second valve space 118' is a return spring 114', which exerts a return force on the piston 113'. Connected into the second valve space 118' is, moreover, a second pressure line 111'', which can be connected either for simple pressure equalization with the environment or with the pneumatic system, in order to supply also the second valve space 118' with a pressurizing medium, so that a second pressure p2 is established in the second valve space 118'.

The movable piston 113' is connected with a push rod 115' guided through a housing wall 119 of the cylindrical valve housing. Push rod 115' acts with its end facing away from the piston 113' essentially radially on the liquid line 160', likewise guided in the housing wall 119 preferably perpendicularly to the push rod 115'. The force, which the push rod 115' exerts on the liquid line 160' results from the force ratio between the force f(p1) exerted by the pressure p1 within the first valve space 118' on the piston 113', the return force of the return spring 114', the force f(p2) exerted by the pressure p2 on the piston 113' reigning in the second valve space 118' and the frictional force f(r), which brakes the movement of the piston 113' in the hollow space of the valve housing.

In FIG. 9 a), valve 152 is shown in its normally closed state. There is essentially no pressure difference between the first pressure line 111' and the second pressure line 111'', i.e. p1 essentially equals p2, in the unactuated, normally closed state. The return spring 114' can in the unactuated state of the valve 152 lie in an uncompressed, equilibrium state. It can, however, also be prestressed with a predetermined force, so that it exerts on the push rod 115' connected with the piston 113' a return force f(s), which is sufficient to collapse the liquid line 160' sufficiently that liquid flow is blocked.

FIG. 9 b) shows valve 152 in the open state. To open valve 152, there is applied via the first pressure line 111' a first pressure p1 different from the second pressure p2 applied via the second pressure line 111'' to the second valve space 118'. The first pressure p1 is so selected that the force acting on the piston 113' because of the first pressure p1 overcomes the frictional force f(r), the return force f(s) of the return spring 114' and the due to the in the second pressure chamber 118' reigning pressure p2 force acting on the piston 113' f(p2), and the piston 113' is shifted sufficiently far from the liquid line 160 that the push rod 115' draws away from the liquid line 160, in order to open liquid line 160, so that liquid can flow through.

Figure 10A:
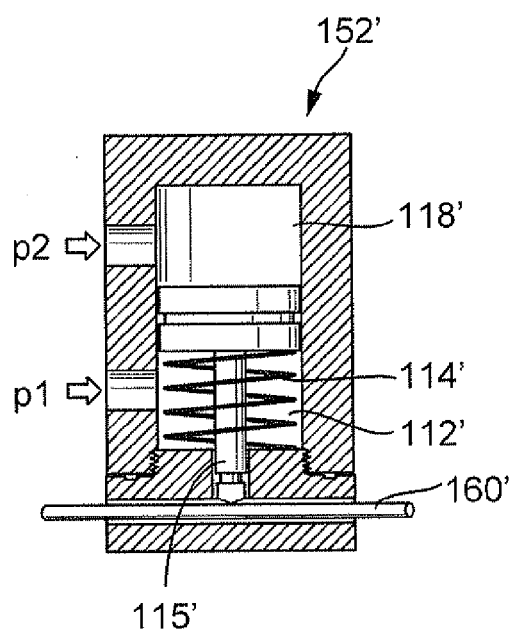
FIG. 10 a) a pneumatically actuatable, normally open, pinch valve in the open state.
Figure 10B:
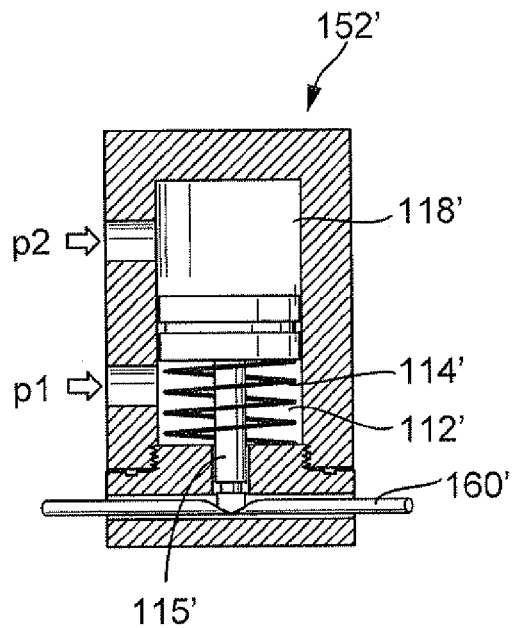

FIGS. 10 a) and b) show a pneumatically actuatable, normally open, pinch valve 152' in the open (a) and in the closed (b) state. It is constructed essentially identically to pinch valve 152 of FIG. 9 and can be used, at least at times, to block liquid transport from a liquid storage unit to the fluidics unit, or from the fluidics unit to the liquid storage unit, when the system 1 is so embodied that the corresponding liquid lines have, at least sectionally, a flexible wall. In contrast to the pinch valve 152 illustrated in FIG. 9, the return spring of the pinch valve 152' is arranged in the first valve space 112' and effects, thus, a return force on the piston 113' against a force exerted on the piston 113' by pressure in the second valve space 118'.

Figure 11:
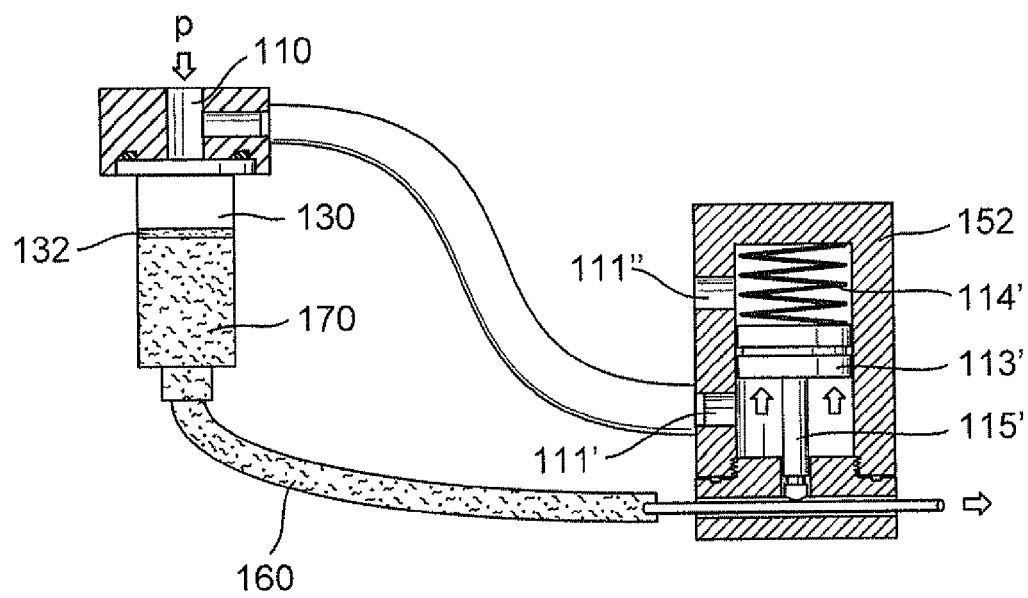
FIG. 11 a liquid storage unit of first type (supply storage unit) with a liquid line to a fluidics unit (not shown) and a pinch valve of FIG. 9 at least at times blocking the liquid line.

FIG. 11 shows a liquid storage unit serving as supply storage unit 130 and leading from this to the fluidics unit (not shown) a liquid line 160, which is embodied, at least partially, as flexible hose, or flexible tubing. The flow of liquid 170 from the liquid storage unit 130 to the fluidics unit (arrow direction) is blockable, at least at times, by a pneumatically actuatable pinch valve 152. The pinch valve 152 is embodied as a normally closed valve of FIGS. 9 a) and b).

Liquid storage unit 130 has in this embodiment a movable piston 132, which divides the liquid storage unit 130 into a liquid space connected with the liquid line 160 and containing the liquid 170, and a gas space connected with the interface 110 for the connection of a pneumatic line for introduction of pressure. The piston 132 lies gas- and liquid sealed in contact with the, for example, cylindrical, inner wall of the liquid storage unit 130. For example, the liquid storage unit in this embodiment can comprise a conventional syringe of glass or plastic material, with a syringe body, especially a cylindrical syringe body, a therein movable, syringe piston contacting the inner wall of the syringe body liquid- and gas tightly, and a syringe nozzle, for example, a conical, syringe nozzle, lying opposite thereto. The syringe piston, especially a shortened syringe piston, serves as a movable piston 132 and the syringe nozzle can be fluidically connected with the liquid line 160.

Since piston 132 seals the liquid storage unit liquid- and gas tightly, a contamination of the stored liquid, for example, by microorganisms, leaking of the gas used for pressure, leaking and evaporation of liquid from the liquid storage unit can all be effectively avoided. Especially advantageous is the application of a conventional syringe, especially a single-use syringe of plastic material with shortened piston. Thus, the application of single-use syringes is very simple to implement. For example, the installation of a syringe filled with liquid before the start-up of the system can be performed safely by a relatively unskilled worker. Also, the installed position need not be defined in the case of application of syringes as liquid storage units.

The liquid storage unit 130 includes, furthermore, an interface 110 for connecting a pneumatic line of a pneumatic unit (not shown), via which a pressurizing medium, e.g. compressed air, or even another liquid, can be fed. The pressure applied by means of the pressurizing medium on the piston 132 effects a shifting of the piston 132, so that liquid 170 is transported from the liquid storage unit 130 into the liquid line 160 toward the fluidics system. Interface 110 is connected in the illustrated example of an embodiment supplementally with the pressure line 111' of the pneumatically actuatable pinch valve 152, via which the first valve space 112' is suppliable with pressure, in order to shift the piston 131' in the direction of the arrows away from the liquid line 160, so that the push rod 115' is pulled back and the liquid line 160 opened. In this way, by pressure loading of the interface 110 with a pressure p, on the one hand, the liquid transport through the liquid line 160 is enabled, while, on the other hand, the piston 132 is moved forwards, so that liquid 170 is transported from the supply storage unit 130 through the liquid line 160 to the fluidics unit.

Figure 12:
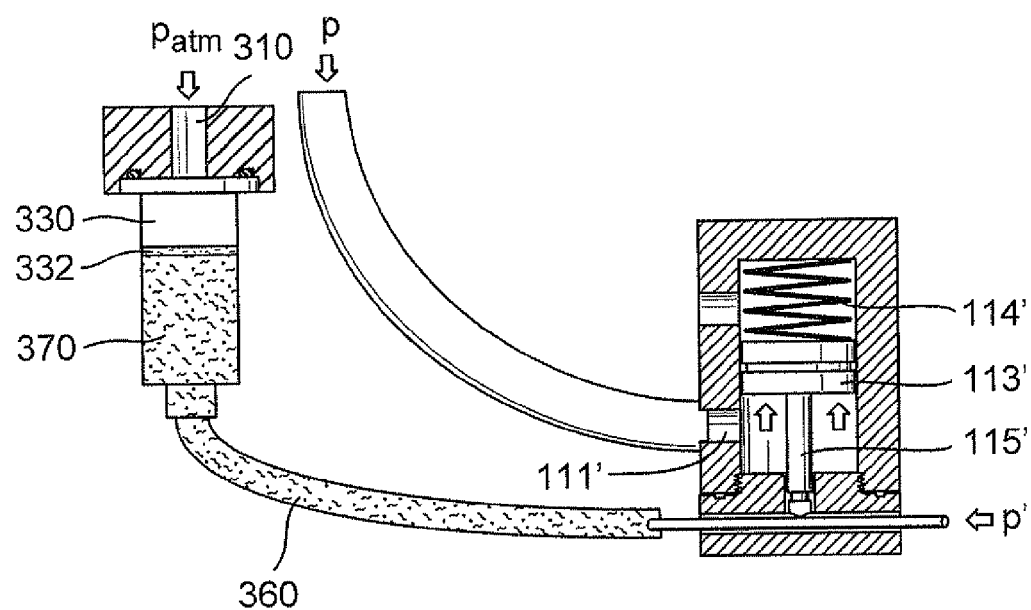
FIG. 12 a liquid storage unit of second type (waste storage unit) with a liquid line coming from a fluidics unit (not shown) and a pinch valve of FIG. 9 at least at times blocking the liquid line.

FIG. 12 shows a liquid storage unit serving as waste storage unit 330, together with a liquid line 360 extending between the waste storage unit 330 and a fluidics unit (not shown). Liquid line 360 is embodied as a flexible hose or flexible tube. Flow of liquid 170 from the fluidics unit toward the waste storage unit 330 (arrow direction) is blockable, at least at times, by a pneumatically actuatable, pinch valve 152. The pinch valve 152 is likewise embodied as a normally closed valve, as was described based on FIGS. 9 a) and b). The waste storage unit 330 includes, same as the supply storage unit 130 shown in FIG. 11, a piston 332 movable within the waste storage unit 330 and liquid- and gas tightly contacting the inner wall of the waste storage unit 330. Piston 332 divides the waste storage unit 330 into a liquid space connected with the liquid line 360 and a gas space connected with the interface 310. Waste storage unit 330 can especially comprise a conventional syringe with a piston 332 terminating the liquid liquid- and gas tightly, which via an interface 310, which can be connected with a pneumatic-line, via which the waste storage unit 330 can be supplied with a pressurizing medium. In the present example, the interface 310 is not supplied by the pneumatic system with pressure, so that always atmospheric pressure is applied to the interface 310 and correspondingly also to the piston 332. If liquid is transported by pressurizing a liquid storage unit of first type of the system (not shown here), analogously as based on FIGS. 2 to 5, from the fluidics unit in arrow direction through the liquid line 360 into the waste storage unit 330, piston 332 moves in the direction of the interface 330, whereby the liquid filled volume of the waste storage unit 330 increases.

Flow of liquid through the liquid line 360 is blocked, at least at times, by the normally closed, pinch valve 152. If it is desired to transport liquid 370 into the waste storage unit 330, a pressure p is applied in the first valve space 112' via a pressure line 111' of the pinch valve 152 connected with the pneumatic system. Pressure p is so selected that it exerts a force on the piston 131' to, as earlier described, overcomes the return force of the return spring 114', the frictional force of the piston 131' and the atmospheric pressure acting on the second pressure line 111", so that the piston 131' moves forward, so that the push rod 115' releases the liquid line 360 and a liquid transport through the liquid line 360 is permit.

The liquid storage units 130, 230, 330, 430 can be embodied as hollow spaces, especially as bores, in the liquid cartridges 100, 200, 300, 400. The liquids can then directly be accommodated in the hollow spaces. In an alternative embodiment, flexible liquid containments can be arranged within the hollow spaces for accommodating the liquids.

Figure 13A:
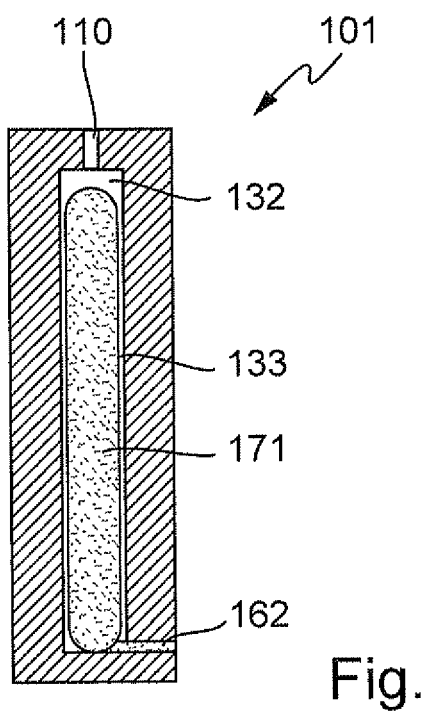
FIG. 13 a) a liquid storage unit with a therein arranged, flexible, liquid container in a first embodiment in the filled state.
Figure 13B:
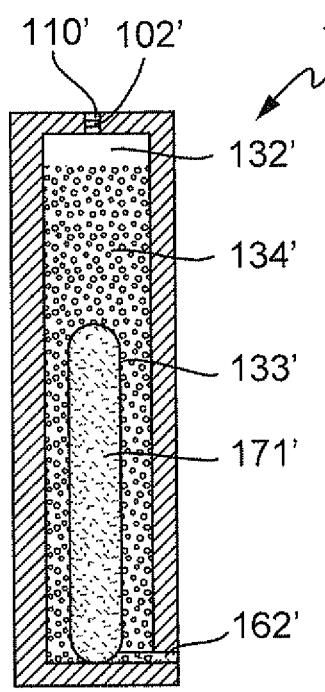
Figure 13C:
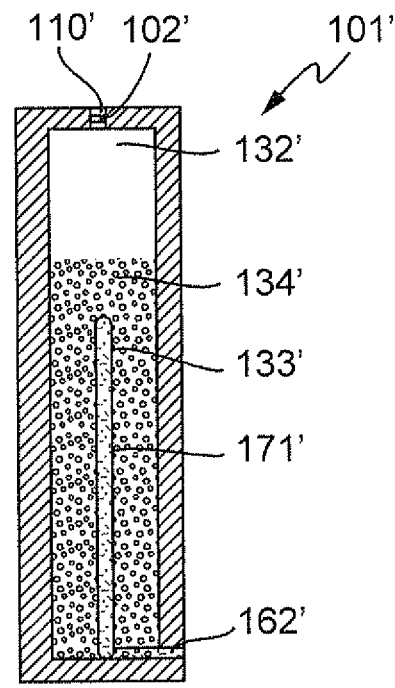

FIG. 13 *a*) shows a liquid cartridge 101 with a liquid storage unit 132, in which a flexible liquid containment embodied as a bag 133 is arranged. Bag 133 is comprises a flexible material, e.g. a plastic foil of, for example, polyethylene or polypropylene. Accommodated in the bag 133 is the liquid 171, for example, a reagent or a waste liquid drained from the fluidics unit. The bag is in fluid connection with a liquid line via a connection 162. The liquid line can be either a liquid supply line 160, 260 for the fluidics unit 500 or a liquid discharge 360, 460 from the fluidics unit 500. The connection 162 of the bag 133 to the liquid line can be formed, for example, by an injection needle, which, in the case of connecting the liquid cartridge 101 via the fluidics interface to the module 3 comprising the fluidics unit 500, pierces through the wall of the bag 133.

When the liquid storage unit 132 is a supply storage unit, supplying the liquid storage unit 132 with pressure via the pneumatic connection 110 of the liquid cartridge 101 can compress the flexible bag 133 and so transfer liquid 171 from the bag 133 via the connection 162 into the liquid supply line connected thereto for the fluidics unit.

In a variant illustrated in FIG. 13 *b*), a liquid cartridge 101' is provided with a flexible bag 133' arranged in the liquid storage unit 132'. The flexible bag 133' contains a liquid 171'. Provided in liquid cartridge 101' as pressurizing medium is a liquid 134'. The liquid storage unit 132' is sealed in this variant by means of a closure element 102', for example, a diaphragm, a membrane or a filter in the pneumatic connection 110', so that, in the case of the separating the pneumatic interface, no liquid 134' can escape into the environment. An introduction of pressure via the pneumatic connection 110' leads via the liquid 134', as in the example of FIG. 13 *a*), to a compressing of the flexible bag 133' and the transfer of liquid 171' from the bag 133' via the connection 162' into the liquid line connected thereto. Advantageously serving as pressurizing medium 134' is an inert liquid with little vapor pressure and high heat capacity, for example, a silicone oil. In this way, liquid loss of the pressurizing medium 134' by evaporation is minimized and a good temperature holding ability of the liquid 171' in the bags assured.

FIG. 13 *c*) shows the liquid cartridge 101' of FIG. 13 *b*) in the almost empty state. Here, corresponding to the volume decrease of the liquid 171' in the bag 133', the liquid level of the liquid 134' serving as pressurizing medium has fallen. Thus, in the case of the embodiment illustrated in FIGS. 13 *b*) and *c*), the remaining amount of liquid 171' in the bag 133' can be ascertained based on the fill level of the liquid 134' serving as pressurizing medium. For this, a fill level sensor can be provided within the liquid storage unit 132'.

In an additional, alternative embodiment, the liquid storage units can also, in each case, comprise a conventional syringe, preferably a single-use syringe of a plastic material with shortened piston, such as are, for example, frequently applied in medicinal applications. The syringe can be sealed to liquid by a movable piston. Such an embodiment is shown, for example, in FIGS. 11 and 12 in combination with pneumatically actuatable valves. Of course, such a liquid storage unit can be applied also in combination with any other valves, especially check valves, in a system for treating liquids.

Liquid can be expelled from such liquid storage units of first type comprising a syringe, serving, for example, as a supply storage unit, by forwards movement of the piston and so be transported into the liquid lines and via these into the fluidics unit. From the fluidics unit, used liquid is transported into the liquid storage units of second type, which serve, for example, as waste storage units, by pressurizing the liquid storage units of first type, as described based on FIGS. 2 to 5. In such case, the piston shifts forwards with increasing liquid volume contained in a liquid storage unit of second type. Based on the forwards movement of the piston, on the one hand, fill levels of liquid storage units of first and/or second type can be ascertain, on the other hand, the forwards movement of one or more pistons of the liquid storage units of first and/or second type can serve for determining the liquid volume transported through the fluidics unit, or a volume- or mass flow through the fluidics unit or a treating unit contained therein.

The invention claimed is:

1. A system for treating liquids, especially for analysis and/or synthesis of liquids, comprising:
   a fluidics unit having at least one functional unit;
   one or more liquid storage units of a first type;
   one or more liquid storage units of a second type;
   first liquid lines, which connect said one or more liquid storage units of the first type and said fluidics unit for supply of liquid from said liquid storage units of the first type into said fluidics unit;
   second liquid lines, which connect said one or more liquid storage units of the second type and said fluidics unit for draining liquid from said fluidics unit into said one or more liquid storage units of the second type;
   first valves; and
   second valves, wherein:
   a flow of liquid through said first liquid lines directed from said fluidics unit to said one or more liquid storage units of the first type is blocked, at least at times, by means of said first valves;
   a flow of liquid through said second liquid lines in the direction from said one or more liquid storage units of the second type to said fluidics unit is blocked, at least at times, by means of said second valves;
   each liquid storage unit of the first type is connected to a pneumatic line of a pneumatic system; and said pneumatic system is embodied in such a manner that a pressure in each pneumatic line is individually adjustable in order to apply predeterminable pressures to the liquid storage units of the first type.

2. The system as claimed in claim 1, wherein:
a flow of liquid through said first liquid lines and/or said second liquid lines and/or through said fluidics unit is producible pneumatically, especially by applying a pressure difference between at least one liquid storage unit of the first type and at least one liquid storage unit of the second type.

3. The system as claimed in claim 1, wherein:
said first and/or said second valves are pneumatically actuated valves.

4. The system as claimed in claim 3, wherein:
each liquid storage unit of the first type has an interface for connecting a pneumatic line, via which each liquid storage unit of the first type can be supplied with pressure; and
said pneumatic line is connected supplementally with a pneumatically actuated, first valve, so that pressure acting on the liquid storage unit of the first type acts simultaneously on the pneumatically actuated, first valve.

5. The system as claimed in claim 1, wherein:
said first and/or said second valves are check valves.

6. The system as claimed in claim 5, wherein:
in each case, a flow path for the transport of liquid from each of said one or more liquid storage units of the first type into said fluidics unit is formed;
and in each flow path a first check valve is arranged in such a manner that its pass through direction points in the flow path toward said fluidics unit; and
in each case, an additional flow path for the transport of liquid from said fluidics unit into each of the one or more liquid storage units of the second type is formed; and
in each additional flow path a second check valve is arranged in such a manner that its pass through direction points in the flow path toward said liquid storage unit of the second type.

7. The system as claimed in claim 1, wherein:
the system includes individual replaceable modules, with a first replaceable module including said fluidics unit; at least one liquid supply line to said fluidics unit and at least one liquid discharge line from said fluidics unit; and
a second replaceable module which includes said one or more liquid storage units of the first type and/or the second type and an interface for connecting said liquid storage units of the first type and/or the second type to said at least one liquid supply line and/or liquid discharge line.

8. The system as claimed in claim 7, wherein:
the second module includes said first and said second valves, especially first and second check valves or first and second pneumatically actuatable valves.

9. The system as claimed in claim 7, wherein:
a second module includes another interface for connecting at least each liquid storage unit of the first type, especially each liquid storage unit of the first and each liquid storage unit of the second type to, in each case, a pneumatic line of a pneumatic system.

10. The system as claimed in claim 9, wherein:
said interface for connecting at least each liquid storage unit of the first type, especially each liquid storage unit, in each case, to a pneumatic line includes a closure element said closure element being one of a diaphragm, a membrane and a filter, and said closure element seals said liquid storage units liquid tightly, but gas permeably.

11. The system as claimed in claim 7, wherein:
said first module and/or said second module includes a heating apparatus, especially a controllable thermoelectric element or a controllable heating element.

12. The system as claimed in claim 1, wherein:
all liquid storage units of the first and the second type, said fluidics unit, all said liquid supply lines from said liquid storage units of the first type to said fluidics unit, and all liquid drain lines from said fluidics unit are combined in a cassette sealed to the environment, especially surrounded by a liquid- and gas sealed housing, and said cassette has an interface for connecting to a pneumatic system.

13. The system as claimed in claim 1, wherein:
the liquid within said liquid storage units of the first type and/or said liquid storage units of the second type is contained, in each case, in a flexible, gaseous-and liquid impermeable containment.

14. The system as claimed in claim 1, wherein:
the system includes at least one flow path for the transport of liquid from one or more liquid storage units of the first type through said fluidics unit into one or more liquid storage units of the second type; and
a measuring arrangement for determining a flow, especially a mass- or volume flow, of the liquid in the flow path.

15. The system as claimed in claim 14, wherein:
the system further includes a control unit, which is embodied, based on at least one of the measured values provided by said measuring arrangement, to control pressure applied to said liquid storage units of the first and the second type.

16. The system as claimed in claim 1, wherein:
said fluidics unit has a first liquid line section connected with a first liquid storage unit of the first type and a second liquid line section connected with a second liquid storage unit of the first type;
said first liquid line section and said second liquid line section combine at a first point to a third liquid line section, which, at a second point of said third liquid line section remote from said first point, branches into a fourth liquid line section and a fifth liquid line section;
at least said fourth liquid line section opens into a functional unit; and
from said functional unit at least a sixth liquid line section leads away, which is connected with a first liquid storage unit of the second type, and said fifth liquid line section is connected with a second liquid storage unit of the second type.

17. The system as claimed in claim 1, wherein:
said fluidics unit is embodied as a microfluidics chip, which includes at least one functional unit and at least one microchannel section leading as a liquid supply line to said functional unit and at least one microchannel section leading as a liquid discharge line away from said functional unit.

18. The system as claimed in claim 1, wherein:
said fluidics unit has only passive elements for controlling the liquid flow.

19. The system as claimed in claim 1, wherein:
each liquid storage unit of the first and each liquid storage unit of the second type is connected to a pneumatic line of said pneumatic system, and said pneumatic system is embodied in such a manner that a pressure in each pneumatic line is individually adjustable in order to apply predeterminable pressures to the liquid storage units of the first and the second type.

20. The system as claimed in claim 1, wherein:
the liquid storage units comprise movable pistons, dividing the liquid storage units into a liquid space connected to a liquid line and a gas space connected with an interface for the connection of a pneumatic line of said pneumatic system.

21. The system as claimed in claim 20, wherein:
the liquid storage units comprise a conventional syringe of glass or plastic material with a syringe body, and a therein movable syringe piston, which contacts the inner wall of the syringe body liquid- and gas tightly, serving as said movable pistons.

22. The system as claimed in claim 1, wherein:
the liquid storage units comprise a conventional syringe of a plastic material with shortened piston.

* * * * *